(12) United States Patent
Ek

(10) Patent No.: US 7,951,163 B2
(45) Date of Patent: May 31, 2011

(54) RETROGRADE EXCISION SYSTEM AND APPARATUS

(75) Inventor: Steven W. Ek, Bolton, MA (US)

(73) Assignee: Arthrosurface, Inc., Franklin, MA (US)

( * ) Notice: Subject to any disclaimer, the term of this patent is extended or adjusted under 35 U.S.C. 154(b) by 934 days.

(21) Appl. No.: 11/551,912

(22) Filed: Oct. 23, 2006

(65) Prior Publication Data

US 2007/0123921 A1    May 31, 2007

Related U.S. Application Data

(63) Continuation-in-part of application No. 11/326,133, filed on Jan. 5, 2006, and a continuation-in-part of application No. 11/209,170, filed on Aug. 22, 2005, and a continuation-in-part of application No. 11/169,326, filed on Jun. 28, 2005, and a continuation-in-part of application No. 10/994,453, filed on Nov. 22, 2004.

(60) Provisional application No. 60/641,552, filed on Jan. 5, 2005, provisional application No. 60/603,473, filed on Aug. 20, 2004, provisional application No. 60/583,549, filed on Jun. 28, 2004, provisional application No. 60/523,810, filed on Nov. 20, 2003.

(51) Int. Cl.
*A61B 17/32* (2006.01)
(52) U.S. Cl. .......................... 606/180; 606/167; 606/170
(58) Field of Classification Search .................... 606/79, 606/80, 96, 167, 180; 408/93, 187, 188, 408/231
See application file for complete search history.

(56) References Cited

U.S. PATENT DOCUMENTS

| 992,819 | A | 5/1911 | Springer |
| 1,451,610 | A | 4/1923 | Gestas |
| 2,267,925 | A | 12/1941 | Johnston |
| 2,570,465 | A | 10/1951 | Lundholm |
| 3,176,395 | A | 4/1965 | Warner et al. |
| 3,840,905 | A | 10/1974 | Deane |

(Continued)

FOREIGN PATENT DOCUMENTS

AU        2001262308        12/2001

(Continued)

OTHER PUBLICATIONS

Bale, MD, Reto J., et al, "Osteochondral Lesions of the Talus: Computer=assisted Retrograde Drilling Feasibility and Accuracy in Initial Experriences[1]", (Radiology. 2001;218:278-282) © RSNA, 2001.

(Continued)

*Primary Examiner* — Thomas C Barrett
*Assistant Examiner* — Christine L Nelson
(74) *Attorney, Agent, or Firm* — Grossman Tucker Perreault & Pfleger PLLC

(57) ABSTRACT

A method for excising a portion of an articular surface using a retrograde procedure. An access tunnel is provided extending through a bone and to the articular surface. A central shaft is inserted through the access tunnel to the articular surface and a cutter is coupled to the central shaft. The cutter is coupled to the central shaft to allow the cutter to rotate with the central and to allow the cutter to be tiltable relative to the central shaft. The cutter is rotated and a retrograde force is applied to the cutter to urge the cutter into the articular surface.

10 Claims, 7 Drawing Sheets

U.S. PATENT DOCUMENTS

| | | | |
|---|---|---|---|
| 4,016,651 A | 4/1977 | Kawahara et al. | |
| 4,034,418 A | 7/1977 | Jackson et al. | |
| 4,044,464 A | 8/1977 | Schiess et al. | |
| 4,158,894 A | 6/1979 | Worrell | |
| 4,344,192 A | 8/1982 | Imbert | |
| 4,433,687 A | 2/1984 | Burke et al. | |
| 4,462,120 A | 7/1984 | Rambert et al. | |
| 4,474,177 A | 10/1984 | Whiteside | |
| 4,484,570 A | 11/1984 | Sutter et al. | |
| 4,531,517 A | 7/1985 | Forte et al. | |
| 4,535,768 A | 8/1985 | Hourahane et al. | |
| 4,634,720 A | 1/1987 | Dorman et al. | |
| 4,655,752 A | 4/1987 | Honkanen et al. | |
| 4,661,536 A | 4/1987 | Dorman et al. | |
| 4,662,371 A | 5/1987 | Whipple et al. | |
| 4,664,669 A | 5/1987 | Ohyabu et al. | |
| 4,673,407 A | 6/1987 | Martin | |
| 4,693,986 A | 9/1987 | Vit et al. | |
| 4,712,545 A | 12/1987 | Honkanen | |
| 4,714,478 A | 12/1987 | Fischer | |
| 4,719,908 A | 1/1988 | Averill et al. | |
| 4,729,761 A | 3/1988 | White | |
| 4,788,970 A | 12/1988 | Kara et al. | |
| 4,823,780 A | 4/1989 | Odensten et al. | |
| 4,842,604 A | 6/1989 | Dorman et al. | |
| 4,896,663 A | 1/1990 | Vandewalls | |
| 4,911,153 A | 3/1990 | Border | |
| 4,920,958 A | 5/1990 | Walt et al. | |
| 4,927,421 A | 5/1990 | Goble et al. | |
| 4,938,778 A | 7/1990 | Ohyabu et al. | |
| 4,940,467 A | 7/1990 | Tronzo | |
| 4,976,037 A | 12/1990 | Hines | |
| 4,978,258 A * | 12/1990 | Lins | 408/187 |
| 4,979,957 A | 12/1990 | Hodorek | |
| 4,989,110 A | 1/1991 | Zevin et al. | |
| 4,990,163 A | 2/1991 | Ducheyne et al. | |
| 4,997,434 A | 3/1991 | Seedhom et al. | |
| 4,998,938 A | 3/1991 | Ghajar et al. | |
| 5,007,930 A | 4/1991 | Dorman et al. | |
| 5,019,104 A | 5/1991 | Whiteside et al. | |
| 5,053,049 A | 10/1991 | Campbell | |
| 5,092,895 A | 3/1992 | Albrektsson et al. | |
| 5,100,405 A | 3/1992 | McLaren | |
| 5,127,920 A | 7/1992 | MacArthur | |
| 5,192,291 A | 3/1993 | Pannek, Jr. | |
| 5,201,881 A | 4/1993 | Evans | |
| 5,211,647 A | 5/1993 | Schmieding | |
| 5,224,945 A | 7/1993 | Pannek, Jr. | |
| 5,255,838 A | 10/1993 | Gladdish, Jr. et al. | |
| 5,263,498 A | 11/1993 | Caspari et al. | |
| 5,263,987 A | 11/1993 | Shah | |
| 5,282,863 A | 2/1994 | Burton | |
| 5,290,313 A | 3/1994 | Heldreth | |
| 5,312,411 A | 5/1994 | Steele | |
| 5,314,478 A | 5/1994 | Oka et al. | |
| 5,314,482 A | 5/1994 | Goodfellow et al. | |
| 5,324,295 A | 6/1994 | Shapiro | |
| 5,336,224 A | 8/1994 | Selman | |
| 5,354,300 A | 10/1994 | Goble et al. | |
| 5,358,525 A | 10/1994 | Fox et al. | |
| 5,360,446 A | 11/1994 | Kennedy | |
| 5,374,270 A | 12/1994 | McGuire et al. | |
| 5,383,937 A | 1/1995 | Mikhail | |
| 5,387,218 A | 2/1995 | Meswania | |
| 5,395,401 A | 3/1995 | Bahler | |
| 5,409,490 A | 4/1995 | Ethridge | |
| 5,409,494 A | 4/1995 | Morgan | |
| 5,413,608 A | 5/1995 | Keller | |
| 5,423,822 A | 6/1995 | Hershberger | |
| 5,458,643 A | 10/1995 | Oka et al. | |
| 5,480,443 A | 1/1996 | Elias | |
| 5,486,178 A | 1/1996 | Hodge | |
| 5,509,918 A | 4/1996 | Romano | |
| 5,520,695 A | 5/1996 | Luckman | |
| 5,522,900 A | 6/1996 | Hollister | |
| 5,534,031 A | 7/1996 | Matsuzaki et al. | |
| 5,540,696 A | 7/1996 | Booth, Jr. et al. | |
| 5,580,353 A | 12/1996 | Mendes et al. | |
| 5,591,170 A | 1/1997 | Spievack et al. | |
| 5,593,450 A | 1/1997 | Scott et al. | |
| 5,595,193 A | 1/1997 | Walus et al. | |
| 5,601,550 A | 2/1997 | Esser | |
| 5,616,146 A | 4/1997 | Murray | |
| 5,620,055 A | 4/1997 | Javerlhac | |
| 5,624,463 A | 4/1997 | Stone et al. | |
| 5,632,745 A | 5/1997 | Schwartz | |
| 5,634,927 A | 6/1997 | Houston et al. | |
| 5,645,598 A | 7/1997 | Brosnahan, III | |
| 5,681,311 A | 10/1997 | Foley et al. | |
| 5,682,886 A | 11/1997 | Delp et al. | |
| 5,683,400 A | 11/1997 | McGuire | |
| 5,683,465 A | 11/1997 | Shinn et al. | |
| 5,683,466 A | 11/1997 | Vitale | |
| 5,700,264 A | 12/1997 | Zucherman et al. | |
| 5,700,265 A | 12/1997 | Romano | |
| 5,702,401 A | 12/1997 | Shaffer | |
| 5,702,465 A | 12/1997 | Burkinshaw | |
| 5,702,467 A | 12/1997 | Gabriel et al. | |
| 5,741,266 A | 4/1998 | Moran et al. | |
| 5,765,973 A * | 6/1998 | Hirsch et al. | 408/188 |
| 5,769,855 A | 6/1998 | Bertin et al. | |
| 5,769,899 A | 6/1998 | Schwartz et al. | |
| 5,771,310 A | 6/1998 | Vannah | |
| 5,776,137 A | 7/1998 | Katz | |
| 5,782,835 A | 7/1998 | Hart et al. | |
| 5,800,440 A | 9/1998 | Stead | |
| 5,810,851 A | 9/1998 | Yoon | |
| 5,817,095 A | 10/1998 | Smith | |
| 5,824,087 A | 10/1998 | Aspden et al. | |
| 5,824,105 A | 10/1998 | Ries et al. | |
| RE36,020 E | 12/1998 | Moore et al. | |
| 5,882,350 A | 3/1999 | Ralph et al. | |
| 5,885,297 A | 3/1999 | Matsen, III | |
| 5,885,298 A | 3/1999 | Herrington et al. | |
| 5,888,210 A | 3/1999 | Draenert | |
| 5,893,889 A | 4/1999 | Harrington | |
| 5,895,390 A | 4/1999 | Moran et al. | |
| 5,911,126 A | 6/1999 | Massen | |
| 5,918,604 A | 7/1999 | Whelan | |
| 5,919,196 A | 7/1999 | Bobic et al. | |
| 5,928,239 A * | 7/1999 | Mirza | 606/79 |
| 5,928,286 A | 7/1999 | Ashby et al. | |
| 5,964,752 A | 10/1999 | Stone | |
| 5,964,768 A | 10/1999 | Huebner | |
| 5,964,808 A | 10/1999 | Blaha et al. | |
| 5,968,050 A | 10/1999 | Torrie | |
| 5,989,269 A | 11/1999 | Vibe-Hansen et al. | |
| 5,990,382 A | 11/1999 | Fox | |
| 5,997,543 A | 12/1999 | Truscott | |
| 5,997,582 A | 12/1999 | Weiss | |
| 6,004,323 A | 12/1999 | Park et al. | |
| 6,010,502 A | 1/2000 | Bagby | |
| 6,015,411 A | 1/2000 | Ohkoshi et al. | |
| 6,017,348 A | 1/2000 | Hart et al. | |
| 6,019,767 A | 2/2000 | Howell | |
| 6,019,790 A | 2/2000 | Holmberg et al. | |
| 6,045,564 A | 4/2000 | Walen | |
| 6,052,909 A | 4/2000 | Gardner | |
| 6,059,831 A | 5/2000 | Braslow | |
| 6,071,310 A | 6/2000 | Picha et al. | |
| 6,081,741 A | 6/2000 | Hollis | |
| 6,086,593 A | 7/2000 | Bonutti | |
| 6,102,948 A | 8/2000 | Brosnahan, III | |
| 6,120,542 A | 9/2000 | Camino et al. | |
| 6,132,433 A | 10/2000 | Whelan | |
| 6,146,385 A | 11/2000 | Torrie et al. | |
| 6,149,654 A | 11/2000 | Johnson | |
| 6,152,960 A | 11/2000 | Pappas | |
| 6,159,216 A | 12/2000 | Burkinshaw et al. | |
| 6,165,223 A | 12/2000 | Metzger et al. | |
| 6,168,626 B1 | 1/2001 | Hyon et al. | |
| 6,171,340 B1 | 1/2001 | McDowell | |
| 6,193,724 B1 | 2/2001 | Chan | |
| 6,206,885 B1 | 3/2001 | Ghahremani et al. | |
| 6,217,549 B1 | 4/2001 | Selmon et al. | |
| 6,217,619 B1 | 4/2001 | Keller | |
| 6,251,143 B1 | 6/2001 | Schwartz et al. | |

| | | |
|---|---|---|
| 6,280,474 B1 | 8/2001 | Cassidy et al. |
| 6,299,645 B1 | 10/2001 | Ogden |
| 6,299,648 B1 | 10/2001 | Doubler et al. |
| 6,306,142 B1 | 10/2001 | Johanson et al. |
| 6,315,798 B1 | 11/2001 | Ashby et al. |
| 6,322,500 B1 | 11/2001 | Sikora et al. |
| 6,328,752 B1 | 12/2001 | Sjostrom et al. |
| 6,342,075 B1 | 1/2002 | MacArthur |
| 6,358,251 B1 | 3/2002 | Mirza |
| 6,358,253 B1 | 3/2002 | Torrie et al. |
| 6,375,658 B1 | 4/2002 | Hangody et al. |
| 6,383,188 B2 | 5/2002 | Kuslich |
| 6,415,516 B1 | 7/2002 | Tirado et al. |
| 6,443,954 B1 | 9/2002 | Bramlet et al. |
| 6,461,373 B2 | 10/2002 | Wyman et al. |
| 6,468,309 B1 | 10/2002 | Lieberman |
| 6,478,801 B1 | 11/2002 | Ralph et al. |
| 6,482,210 B1 | 11/2002 | Skiba et al. |
| 6,494,914 B2 | 12/2002 | Brown |
| 6,520,964 B2 | 2/2003 | Tallarida et al. |
| 6,527,754 B1 | 3/2003 | Tallarida et al. |
| 6,530,956 B1 | 3/2003 | Mansmann |
| 6,540,786 B2 | 4/2003 | Chibrac et al. |
| 6,551,322 B1 | 4/2003 | Lieberman |
| 6,554,866 B1 | 4/2003 | Aicher et al. |
| 6,575,982 B1 | 6/2003 | Bonutti |
| 6,585,666 B2 | 7/2003 | Suh et al. |
| 6,591,581 B2 | 7/2003 | Schmieding |
| 6,599,321 B2 | 7/2003 | Hyde et al. |
| 6,607,561 B2 | 8/2003 | Brannon |
| 6,610,067 B2 | 8/2003 | Tallarida |
| 6,626,950 B2 | 9/2003 | Brown et al. |
| 6,679,917 B2 | 1/2004 | Ek |
| 6,746,451 B2 | 6/2004 | Middleton et al. |
| 6,755,837 B2 * | 6/2004 | Ebner .............. 606/84 |
| 6,770,078 B2 | 8/2004 | Bonutti |
| 6,783,550 B2 | 8/2004 | MacArthur |
| 6,783,551 B1 | 8/2004 | Metzger |
| 6,802,864 B2 | 10/2004 | Tornier |
| 6,814,735 B1 | 11/2004 | Zirngibl |
| 6,827,722 B1 | 12/2004 | Schoenefeld |
| 6,860,902 B2 | 3/2005 | Reiley |
| 6,884,246 B1 | 4/2005 | Sonnabend et al. |
| 6,893,467 B1 | 5/2005 | Bercovy |
| 6,923,813 B2 | 8/2005 | Phillips et al. |
| 6,926,739 B1 | 8/2005 | O'Connor |
| 6,962,577 B2 | 11/2005 | Tallarida et al. |
| 6,969,393 B2 | 11/2005 | Pinczewski et al. |
| 6,984,248 B2 | 1/2006 | Hyde, Jr. |
| 6,989,016 B2 | 1/2006 | Tallarida et al. |
| 7,029,479 B2 | 4/2006 | Tallarida |
| 7,063,717 B2 | 6/2006 | St. Pierre et al. |
| 7,115,131 B2 | 10/2006 | Engh et al. |
| 7,156,880 B2 | 1/2007 | Evans et al. |
| 7,160,305 B2 | 1/2007 | Schmieding |
| 7,163,541 B2 | 1/2007 | Ek |
| 7,166,133 B2 | 1/2007 | Evans et al. |
| 7,192,431 B2 | 3/2007 | Hangody et al. |
| 7,204,839 B2 | 4/2007 | Dreyfuss et al. |
| 7,204,854 B2 | 4/2007 | Guederian et al. |
| 7,235,107 B2 | 6/2007 | Evans et al. |
| 7,238,189 B2 | 7/2007 | Schmieding et al. |
| 7,241,316 B2 | 7/2007 | Evans et al. |
| 7,264,634 B2 | 9/2007 | Schmieding |
| 7,290,347 B2 | 11/2007 | Augostino et al. |
| 7,303,577 B1 | 12/2007 | Dean |
| 7,311,702 B2 | 12/2007 | Tallarida et al. |
| 7,361,195 B2 | 4/2008 | Schwartz et al. |
| 7,510,558 B2 | 3/2009 | Tallarida |
| 7,569,059 B2 | 8/2009 | Cerundolo |
| 7,641,658 B2 | 1/2010 | Shaolian et al. |
| 2001/0012967 A1 | 8/2001 | Mosseri |
| 2001/0039455 A1 | 11/2001 | Simon et al. |
| 2001/0056266 A1 | 12/2001 | Tallarida et al. |
| 2002/0055783 A1 | 5/2002 | Tallarida et al. |
| 2002/0106393 A1 | 8/2002 | Bianchi et al. |
| 2002/0138150 A1 | 9/2002 | Leclercq |
| 2002/0147498 A1 | 10/2002 | Tallarida et al. |
| 2003/0028196 A1 | 2/2003 | Bonutti |
| 2003/0060887 A1 | 3/2003 | Ek |
| 2003/0065391 A1 | 4/2003 | Re et al. |
| 2003/0100953 A1 | 5/2003 | Rosa et al. |
| 2003/0105465 A1 | 6/2003 | Schmieding et al. |
| 2003/0120276 A1 | 6/2003 | Tallarida et al. |
| 2003/0120278 A1 | 6/2003 | Morgan et al. |
| 2003/0130741 A1 | 7/2003 | McMinn |
| 2003/0171756 A1 | 9/2003 | Fallin et al. |
| 2003/0181878 A1 | 9/2003 | Tallarida et al. |
| 2003/0204195 A1 | 10/2003 | Keane et al. |
| 2003/0216669 A1 | 11/2003 | Lang et al. |
| 2003/0225456 A1 | 12/2003 | Ek |
| 2003/0225457 A1 | 12/2003 | Justin et al. |
| 2004/0015170 A1 | 1/2004 | Tallarida et al. |
| 2004/0034359 A1 | 2/2004 | Schmieding et al. |
| 2004/0034437 A1 | 2/2004 | Schmieding |
| 2004/0082906 A1 | 4/2004 | Tallarida et al. |
| 2004/0106928 A1 | 6/2004 | Ek |
| 2004/0133276 A1 | 7/2004 | Lang et al. |
| 2004/0138754 A1 | 7/2004 | Lang et al. |
| 2004/0138758 A1 | 7/2004 | Evans et al. |
| 2004/0148030 A1 | 7/2004 | Ek |
| 2004/0153087 A1 | 8/2004 | Sanford et al. |
| 2004/0167632 A1 | 8/2004 | Wen et al. |
| 2004/0193281 A1 | 9/2004 | Grimes |
| 2004/0199166 A1 | 10/2004 | Schmieding et al. |
| 2004/0210309 A1 | 10/2004 | Denzer et al. |
| 2004/0220574 A1 | 11/2004 | Pelo et al. |
| 2004/0230315 A1 | 11/2004 | Ek |
| 2004/0260303 A1 | 12/2004 | Carrison |
| 2005/0015153 A1 | 1/2005 | Gobel et al. |
| 2005/0038520 A1 | 2/2005 | Binette et al. |
| 2005/0043805 A1 | 2/2005 | Chudik |
| 2005/0043808 A1 | 2/2005 | Felt et al. |
| 2005/0065612 A1 | 3/2005 | Winslow |
| 2005/0075642 A1 | 4/2005 | Felt |
| 2005/0143731 A1 | 6/2005 | Justin et al. |
| 2005/0143745 A1 | 6/2005 | Hodorek et al. |
| 2005/0143831 A1 | 6/2005 | Justin et al. |
| 2005/0154398 A1 | 7/2005 | Miniaci et al. |
| 2005/0209705 A1 | 9/2005 | Niederauer et al. |
| 2005/0229323 A1 | 10/2005 | Mills et al. |
| 2005/0287187 A1 | 12/2005 | Mansmann |
| 2006/0004461 A1 | 1/2006 | Justin et al. |
| 2006/0020343 A1 | 1/2006 | Ek |
| 2006/0052878 A1 | 3/2006 | Schmieding |
| 2006/0058744 A1 | 3/2006 | Tallarida et al. |
| 2006/0058883 A1 | 3/2006 | Aram et al. |
| 2006/0085006 A1 | 4/2006 | Ek |
| 2006/0149370 A1 | 7/2006 | Schmieding et al. |
| 2006/0190002 A1 | 8/2006 | Tallarida |
| 2006/0195112 A1 | 8/2006 | Ek |
| 2006/0229726 A1 | 10/2006 | Ek |
| 2007/0005143 A1 | 1/2007 | Ek |
| 2007/0038307 A1 | 2/2007 | Webster et al. |
| 2007/0073394 A1 | 3/2007 | Seedhom et al. |
| 2007/0093842 A1 | 4/2007 | Schmieding |
| 2007/0093890 A1 | 4/2007 | Eliasen et al. |
| 2007/0118136 A1 | 5/2007 | Ek |
| 2007/0179608 A1 | 8/2007 | Ek |
| 2007/0233128 A1 | 10/2007 | Schmieding et al. |
| 2007/0250067 A1 | 10/2007 | Schmieding et al. |
| 2007/0255399 A1 | 11/2007 | Eliasen et al. |
| 2007/0265700 A1 | 11/2007 | Eliasen et al. |
| 2007/0288031 A1 | 12/2007 | Dreyfuss et al. |
| 2007/0299519 A1 | 12/2007 | Schmieding |
| 2008/0004659 A1 | 1/2008 | Burkhart et al. |
| 2008/0015709 A1 | 1/2008 | Evans et al. |
| 2008/0027430 A1 | 1/2008 | Montgomery et al. |
| 2008/0033443 A1 | 2/2008 | Sikora et al. |
| 2008/0086139 A1 | 4/2008 | Bourke et al. |
| 2008/0172125 A1 | 7/2008 | Ek |
| 2008/0183290 A1 | 7/2008 | Baird et al. |
| 2008/0188935 A1 | 8/2008 | Saylor et al. |
| 2008/0275512 A1 | 11/2008 | Albertirio et al. |
| 2008/0306483 A1 | 12/2008 | Iannarone |
| 2009/0198288 A1 | 8/2009 | Hoof et al. |
| 2009/0234452 A1 | 9/2009 | Steiner et al. |
| 2011/0009964 A1 | 1/2011 | Schwartz et al. |

FOREIGN PATENT DOCUMENTS

| | | |
|---|---|---|
| AU | 2003262428 | 8/2009 |
| DE | 2933174 | 4/1980 |
| DE | 3516743 | 11/1986 |
| DE | 3840466 | 6/1990 |
| EP | 0241240 | 10/1987 |
| EP | 0350780 | 7/1989 |
| EP | 0350780 | 1/1990 |
| EP | 0485678 | 5/1992 |
| EP | 0327387 | 9/1992 |
| EP | 0505634 | 9/1992 |
| EP | 0903125 | 3/1999 |
| EP | 0903127 | 3/1999 |
| EP | 0661023 | 8/2001 |
| EP | 1426013 | 9/2004 |
| EP | 1278460 | 4/2009 |
| FR | 2242068 | 3/1975 |
| FR | 2642301 | 3/1990 |
| FR | 2676917 | 12/1992 |
| FR | 2693650 | 1/1994 |
| FR | 2718014 | 10/1995 |
| FR | 2733904 | 11/1996 |
| FR | 2739151 | 3/1997 |
| GB | 2372707 | 9/2002 |
| JP | 61502029 | 9/1986 |
| JP | 63300758 | 12/1988 |
| JP | 3504932 | 10/1991 |
| JP | H03-092328 | 11/1992 |
| JP | 518511 | 3/1993 |
| JP | 06339490 | 12/1994 |
| JP | 11244315 | 9/1999 |
| JP | 2001525210 | 12/2001 |
| JP | 2002291779 | 10/2002 |
| JP | 2003534096 | 11/2003 |
| WO | 8803781 | 6/1988 |
| WO | 8909578 | 10/1989 |
| WO | 9427507 | 12/1994 |
| WO | 9624304 | 8/1996 |
| WO | 9722306 | 6/1997 |
| WO | 0105336 | 1/2001 |
| WO | 0166021 | 9/2001 |
| WO | 0166022 | 9/2001 |
| WO | 0182677 | 11/2001 |
| WO | 0191648 | 12/2001 |
| WO | 0191672 | 12/2001 |
| WO | 0217821 | 3/2002 |
| WO | 02086180 | 10/2002 |
| WO | 03047470 | 6/2003 |
| WO | 03051210 | 6/2003 |
| WO | 03051211 | 6/2003 |
| WO | 03061516 | 7/2003 |
| WO | 03065909 | 8/2003 |
| WO | 2004014261 | 2/2004 |
| WO | 2004026170 | 4/2004 |
| WO | 2004052216 | 6/2004 |
| WO | 2004075777 | 9/2004 |
| WO | 2005051231 | 6/2005 |
| WO | 2005512331 | 6/2005 |
| WO | 2006004885 | 1/2006 |
| WO | 2006091686 | 8/2006 |

OTHER PUBLICATIONS

Biomet/Copeland, "Aequalis® Resurfacing Head" Tornier, Scientific Vision, Surgical Leadership, SS-401 Jan. 2007.

Kumai, M.D., Tsukasa, et al Arthroscopic Drilling for the Treatment of Osteochondral Lesions of the Talus, The Journal of Bone & Joint Surgery, American vol. 81:1229-35(1999).

Matsusue, M.D., Yoshitaka, et al, "Arthroscopic Osteochondral Autograft Transplantation for Chondral Lesion of the Tibial Plateau of the Knee", Arthroscopy: The Journal of Arthroscopic and Related Surgery, vol. 17, No. 6 (Jul.-Aug.), 2001:pp. 653-659.

Pill M.S., P.T., Stephan G. et al, "Osteochondritis Dissecans of the Knee: Experiences at the Children's Hospital of Philadelphia and a Review of Literature", the University of Pennsylvania Orthopaedic Journal 14: 25-33, 2001.

Schneider, T., et al, "Arthroscopy of the ankle joint. A list of indications and realistic expectations", Foot and Ankle Surgery 1996 2:189-193, © 1996 Arnette Blackwell SA.

Taranow WS, et al, "Retrograde drilling of osteochondral lesions of the medial talar dome", PubMed, www.pubmed.gov, A service of the National Library of Medicing and the Natinal Institutes of Health, Foot Ankle Int. Aug. 1999;20 (8):474-80.

Ueblacker, M.D., Peter, et al, "Retrograde Cartilage Transplantation of the Proximal and Distal Tibia", Arthroscopy: The Journal of Arthroscipic and Related Surgery, vol. 20, No. 1 (January), 2004: pp. 73-78.

Notice of Reasons for Rejection issued in related Japanese Patent Application No. 2003-394702 mailed Jul. 21, 2009.

Notice of Reasons for Rejection issued in related Japanese Patent Application No. 20-541615 mailed May 26, 2009.

International Preliminary Report on Patentability issued in related International Patent Application No. PCT/US2007/025284 dated Jun. 25, 2009.

Office Action issued in related Australian Patent Application No. 2007216648 dated Jul. 28, 2009.

European Search Report dated Jul. 10, 2009 issued in related European Patent Application No. 09002088.4.

International Preliminary Report on Patentability and Written Opinion dated May 22, 2006 in corresponding PCT patent application No. PCT/US04/039181.

International Preliminary Report on Patentability and Written Opinion dated May 22, 2006 in corresponding PCT patent application No. PCT/US04/039181.

Canadian Office Action dated Jan. 2, 2008 issued in corresponding Canadian Application No. 2407440.

International Preliminary Report on Patentability and Written Opinion dated Jun. 19, 2007 in corresponding PCT patent application No. PCT/US2005/005980.

International Preliminary Report on Patentability and Written Opinion dated Jul. 10, 2007 in corresponding PCT patent application No. PCT/US2006/000380.

International Search Report dated Dec. 21, 2001 issued in corresponding PCT patent application No. PCT/US01/14061.

International Search Report dated Nov. 12, 2002 issued in corresponding PCT patent application No. PCT/US01/48821.

International Search Report dated May 23, 2003 issued in corresponding PCT patent application No. PCT/US02/40310.

International Search Report and Written Opinion dated Dec. 30, 2004 issued in corresponding PCT patent application No. PCT/US04/05539.

International Search Report and Written Opinion dated Jan. 30, 2006 issued in corresponding PCT patent application No. PCT/US04/39181.

International Search Report and Written Opinion dated Aug. 30, 2006 issued in corresponding PCT patent application No. PCT/US06/06323.

International Search Report and Written Opinion dated Nov. 27, 2006 issued in corresponding PCT patent application No. PCT/US06/00380.

International Search Report and Written Opinion dated May 22, 2007 issued in corresponding PCT patent application No. PCT/US05/05980.

International Search Report and Written Opinion dated Aug. 8, 2007 issued in corresponding PCT patent application No. PCT/US06/29875.

English language translation of Japanese Office Action dated Aug. 9, 2007 issued in corresponding Japanese application No. 2003-552148.

United States Office Action issued is related U.S. Appl. No. 10/760,965 dated Feb. 19, 2008.

Australian Office Action issued in related Australian Patent Application No. 2003262428 dated Mar. 20, 2008.

Australian Office Action issued in related Australian Patent Application No. 2004293042 dated Feb. 20, 2008.

International Preliminary Report on Patentability dated Mar. 1, 2007 received in corresponding International Patent Application No. PCT/US2005/030120 (6 pages).

USPTO Office Action dated Dec. 21, 2007 issued in corresponding U.S. Appl. No. 11/169,326.

USPTO Office Action dated Dec. 26, 2007 issued in U.S. Appl. No. 11/379,151.

USPTO Office Action dated Oct. 9, 2007 issued in U.S. Appl. No. 10/373,463.
USPTO Office Action dated Aug. 29, 2007 issued in U.S. Appl. No. 10/760,965.
USPTO Office Action dated May 31, 2007 issued in corresponding U.S. Appl. No. 11/326,133.
USPTO Office Action dated Apr. 26, 2007 issued in U.S. Appl. No. 10/373,463.
USPTO Office Action dated Apr. 4, 2007 issued in corresponding U.S. Appl. No. 10/789,545.
USPTO Office Action dated Mar. 15, 2007 issued in U.S. Appl. No. 10/760,965.
USPTO Office Action dated Feb. 20, 2007 issued in corresponding U.S. Appl. No. 11/326,133.
USPTO Office Action dated Nov. 6, 2006 issued in U.S. Appl. No. 10/760,965.
USPTO Office Action dated Oct. 17, 2006 issued in U.S. Appl. No. 10/373,463.
USPTO Office Action dated Oct. 31, 2006 issued in U.S. Appl. No. 10/760,965.
USPTO Office Action dated Jul. 25, 2006 issued in U.S. Appl. No. 10/760,965.
USPTO Office Action dated May 10, 2006 issued in corresponding U.S. Appl. No. 10/373,463.
USPTO Office Action dated Apr. 21, 2006 issued in corresponding U.S. Appl. No. 10/308,718.
USPTO Office Action dated Nov. 9, 2005 issued in corresponding U.S. Appl. No. 10/308,718.
USPTO Office Action dated Dec. 8, 2005 issued in corresponding U.S. Appl. No. 10/373,463.
USPTO Office Action dated Aug. 31, 2005 issued in corresponding U.S. Appl. No. 10/308,718.
USPTO Office Action dated Aug. 16, 2005 issued in corresponding U.S. Appl. No. 10/373,463.
USPTO Office Action dated Jan. 27, 2005 issued in corresponding U.S. Appl. No. 10/373,463.
USPTO Office Action dated Aug. 13, 2004 issued in corresponding U.S. Appl. No. 10/373,463.
USPTO Notice of Allowance issued Sep. 26, 2003 in U.S. Appl. No. 10/162,533.
USPTO Notice of Allowance issued May 12, 2003 in U.S. Appl. No. 10/024,077.
USPTO Office Action dated Apr. 1, 2003 issued in U.S. Appl. No. 10/162,533.
USPTO Office Action dated Mar. 28, 2003 issued in corresponding U.S. Appl. No. 10/024,077.
USPTO Notice of Allowance issued Sep. 30, 2002 in U.S. Appl. No. 09/846,657.
USPTO Office Action dated Apr. 2, 2002 issued in corresponding U.S. Appl. No. 09/846,657.
USPTO Office Action dated Feb. 27, 2002 issued in corresponding U.S. Appl. No. 09/846,657.
STD00.01 USPTO Office Action dated Jan. 3, 2002 issued in corresponding U.S. Appl. No. 09/846,657.
AU Examiners report dated Jan. 18, 2006 issued in corresponding Australian patnet application No. 2005202099.
AU Examiners report dated Jan. 12, 2007 issued in corresponding Australian patnet application No. 2006202337.
AU Examiners report dated Feb. 21, 2007 issued in corresponding Australian patnet application No. 2005202099.
AU Examiners report dated May 23, 2007 issued in corresponding Australian patnet application No. 2005202099.
AU Notice of Acceptance dated Aug. 6, 2007 in Patent Application No. 20022357284.
EPO supplementary partial search report dated May 10, 2004 issued in corresponding European application 01932833.5-231-/US0114061.
EPO supplementary search report dated Aug. 30, 2004 issued in corresponding European application 01932833.5.
EPO Office Action dated Aug. 23, 2004, received in related EPO application No. 03 026 286.9 (4 pgs).
EPO Office Action dated Mar. 15, 2005, received in related EPO application No. 03 026 286.9 (3 pgs).

EPO Search Report received in related EPO Application No. 03 02 6286.9 dated Feb. 26, 2004 (5pgs).
EPO Search Report received in related EPO Application No. 03 02 6286.9 dated Apr. 27, 2004 (6pgs).
Examination Report dated Feb. 22, 2005 received in corresponding European Application No. 10932833.5 (3pages).
EPO Office Action dated Sep. 22, 2005 issued in corresponding European application 01932833.5-2310.
EPO Office Action dated Sep. 11, 2006 issued in corresponding European application 01932833.5-2310.
European Commnication pursuant to Article 96(2) EPC dated Sep. 11, 2006 received in corresponding Eurpoean Patent Application Serial No. 01 932 833.5.
International Preliminary Examination Report dated Nov. 29, 2001 issued in corresponding PCT patent application No. PCT/US01/1406.
International Preliminary Examination Report dated Nov. 5, 2002 issued in corresponding PCT patent application No. PCT/US01/1406.
International Preliminary Examination Report dated Nov. 12, 2002 issued in corresponding PCT patent application No. PCT/US01/48821.
International Preliminary Examination Report dated Sep. 12, 2003 issued in corresponding PCT patent application No. PCT/US02/40310.
International Preliminary Examination Report dated Oct. 27, 2003 issued in corresponding PCT patent application No. PCT/US01/48821.
International Preliminary Examination Report dated Aug. 19, 2004 issued in corresponding PCT patent application No. PCT/US02/40310.
International Preliminary Report on Patentability dated Aug. 20, 2009 issued in related International Patent Application No. 2008053194.
Notice of Allowance dated Aug. 25, 2009 issued in related U.S. Appl. No. 11/379,151.
Notice of Allowance dated Aug. 27, 2009 issued in related U.S. Appl. No. 10/760,965.
U.S. Office Action dated Jan. 9, 2009 issued in related U.S. Appl. No. 10/373,463.
Canadian Office Action dated Dec. 9, 2008 issued in related Canadian Patent Application No. 2407440.
Supplemental European Search Report dated Nov. 6, 2008 issued in related European Patent Application No. 05791453.3-2310.
Japanese Office Action dated Dec. 19, 2008 issued in Japanese Patent Application No. 2006501193.
Japanese Office Action dated Jan. 13, 2009 issued in Japanese Patent Application No. 2003552147.
International Search Report dated Jan. 30, 2006 issued in related International Patent Application No. PCT/US04/39181.
U.S. Office Action dated Mar. 27, 2009 issued in related U.S. Appl. No. 11/169,326.
European Office Action dated Feb. 26, 2009 in related European Patent Application No, 05791453.3.
International Search Report with Written Opinion dated Sep. 29, 2006 received in corresponding International Patent Application Serial No. PCT/US05/30120 (9 pages).
McCarty, III, et al., "Nonarthroplasty Treatment of Glenohumeral Cartilage Lesions," Arthroscopy, The Journal of Arthroscopic and related Surgery, vol. 21, No. 9; Sep. 2005 (pp. 1131-1142).
Bushnell, et al., "Bony Instability of the Shoulder," Arthroscopy, The Journal of Arthroscopic and related Surgery, vol. 24, No. 9; Sep. 2005 (pp. 1061-1073).
Scalise, et al., "Resurfacing Arthroplasty of the Humerus: Indications, Surgical Technique, and Clinical Results," Techniques in Shoulder and Elbow Surgery 8(3):152-160; 2007.
Davidson, et al., "Focal Anatomic Patellofemoral Inlay Resurfacing: Theoretic Basis, Surgical Technique, and Case Reports," Orthop. Clin. N. Am., 39 (2008) pp. 337-346.
Provencher, et al., "Patellofemoral Kinematics After Limited Resurfacing of the Trochlea," The Journal of Knee Surgery, vol. 22 No. 2 (2008) pp. 1-7.

Dawson, et al., "The Management of Localized Articular Cartilage Lesions of the Humeral Head in the Athlete," Operative Techniques in Sports Medicine, vol. 16, Issue 1, pp. 14-20 (2008).
Uribe, et al., "Partial Humeral Head Resurfacing for Osteonecrosis," Journal of Shoulder and Elbow Surgery, (2009) 6 pages.
Burks, "Implant Arthroplasty of the First Metatarsalphalangeal Joint," Clin. Podiatr. Med. Surg., 23 (2006) pp. 725-731.
Hasselman, et al., "Resurfacing of the First Metatarsal Head in the Treatment of Hallux Rigidus," Techniques in Foot & Ankle Surgery 7(1):31-40, 2008.
Gelenkoberflachen, et al., "Partial hemi-resurfacing of the hip joint—a new approach to treat local osteochondral defects?" Biomed Tech 2006; 51:371-376 (2006).
Sullivan, "Hallux Rigidus: MTP Implant Arthroplasty," Foot Ankle Clin. N. Am. 14 2009) pp. 33-42.
Cook, et al., "Meta-analysis of First Metatarsophalangeal Joint Implant Arthroplasty," Journal of Foot and Ankle Surgery, vol. 48, Issue 2, pp. 180-190 (2009).
Derner, "Complications and Salvage of Elective Central Metatarsal Osteotomies," Clin. Podiatr. Med. Surg. 26 (2009) 23-35.
Kirker-Head, et al., "Safety of, and Biological Functional Response to, a Novel Metallic Implant for the Management of Focal Full-Thickness Cartilage Defects: Preliminary Assessment in an Animal Model Out to 1 year," Journal of Orthopedic Research, May 2006 pp. 1095-1108.
Beecher, et al. "Effects of a contoured articular prosthetic device on tibiofemoral peak contact pressure: a biomechanical study," Knee Surg Sports Traumatol Arthrosc. Jan. 2008; 16(1): 56-63.
United States Office Action dated May 13, 2009 issued in related U.S. Appl. No. 11/359,892.
United States Office Action dated May 8, 2009 issued in related U.S. Appl. No. 11/209,170.
United States Office Action dated May 1, 2009 issued in related U.S. Appl. No. 11/461,240.
Australian Office Action dated Jan. 29, 2009 issued in related Australian Patent Application No. 2004216106.
European Search Report dated Apr. 22, 2009 issued in related European Patent Application No. 09002088.4.
U.S. Office Action issued in related U.S. Appl. No. 11/326,133 dated Jun. 12, 2008.
International Search Report and Written Opinion dated Jun. 24, 2008 issued in related International Patent Application No. PCT/US07/73685.
International Search Report and Written Opinion dated Jun. 11, 2008 issued in related International Patent Application No. PCT/US07/25284.
International Search Report and Written Opinion dated Aug. 8, 2008 issued in related International Patent Application No. PCT/US08/53988.
U.S. Office Action issued in related U.S. Appl. No. 10/994,453 dated Jun. 5, 2007.
Japanese Office Action dated Jul. 22, 2008 issued in related Japanese Patent Application No. 2006-501193.
U.S. Office Action issued in related U.S. Appl. No. 10/373,463 dated Apr. 21, 2008.
Notice Of Allowance received in U.S. Appl. No. 10/618,887 dated Aug. 15, 2008.
Australia Office Action issued in related Australian Patent Application No. 2007216648 dated May 30, 2008.
European Office Action issued in related European Patent Application No. 01932833.5-2310 dated Apr. 25, 2008.
U.S. Office Action received in related U.S. Appl. No. 11/169,326 dated Jun. 30, 2008.
U.S. Office Action received in related U.S. Appl. No. 11/169,326 dated Jul. 27, 2007.
U.S. Office Action received in related U.S. Appl. No. 11/169,326 dated Apr. 17, 2007.
U.S. Office Action received in related U.S. Appl. No. 11/169,326 dated Mar. 9, 2007.
Canadian Office Action issued in related Canadian Patent Application No. 2546582 dated Aug. 21, 2008.
U.S. Office Action issued in related U.S. Appl. No. 10/994,453 dated Sep. 3, 2008.
U.S. Office Action dated Oct. 21, 2008 issued in related U.S. Appl. No. 11/461,240.
U.S. Office Action dated Jun. 25, 2008 issued in related U.S. Appl. No. 11/359,891.
U.S. Office Action dated Sep. 25, 2008 issued in related U.S. Appl. No. 11/326,133.
U.S. Office Action dated Jul. 2, 2008 issued in related U.S. Appl. No. 11/379,151.
European Office Action dated Oct. 6, 2008 issued in related European Patent Application No. 01932833.5-2310.
U.S. Office Action dated Jun. 27, 2008 issued in related U.S. Appl. No. 10/760,965.
International Search Report and Written Opinion dated Oct. 1, 2008 issued in related International Patent Application No. PCT/US08/53194.
International Search Report and Written Opinion dated Oct. 9, 2008 issued in related International Patent Application No. PCT/US07/82262.
European Search Report dated Nov. 4, 2008 issued in related European Patent Application No. 04811836.8-2310.
Habermeyer, "Eclipse, Schaftfreie Schulterprothese Operationsanleitung," (dated unknown).
U.S. Office Action dated Aug. 30, 2006 issued in related U.S. Appl. No. 10/618,887.
U.S. Office Action dated Jan. 15, 2008 issued in related U.S. Appl. No. 10/618,887.
U.S. Office Action dated May 18, 2009 issued in related U.S. Appl. No. 11/209,170.
U.S. Office Action dated May 28, 2009 issued in related U.S. Appl. No. 11/359,891.
U.S. Office Action dated May 11, 2009 issued in related U.S. Appl. No. 11/359,892.
International Search Report and Written Opinion dated Jun. 1, 2009 issued in related International Patent Application No. PCT/US2009/035889.
International Preliminary Report and Patentability dated May 7, 2009 issued in related International Patent Application No. PCT/US2007/082262.
Supplemental European Search Report dated May 28, 2009 issued in related International European Patent Application No. 01997077.1.
Supplemental European Search Report dated May 11, 2009 issued in related International European Patent Application No. 02805182.9.
Notice of Allowance dated Feb. 20, 2009 issued in related U.S. Appl. No. 10/618,887.
Notice of Allowance issued in corresponding U.S. Appl. No. 10/618,887 dated Sep. 13, 2007.
Notice of Allowance issued in corresponding U.S. Appl. No. 10/308,718 dated Sep. 11, 2006.
Office Action issued in corresponding U.S. Appl. No. 11/326,133 dated Oct. 17, 2007.
Office Action issued in corresponding U.S. Appl. No. 10/741,044 dated Oct. 26, 2005.
International Search Report with Written Opinion dated Nov. 29, 2006 received in corresponding International Patent Application Serial No. PCT/US05/23200 (7 pages).
Supplemental Notice of Allowance dated Nov. 25, 2009 issued in related U.S. Appl. No. 10/373,463.
Office Action dated Dec. 24, 2009 issued in related U.S. Appl. No. 10/994,453.
Notice of Reasons for Rejection dated Nov. 17, 2009 issued in Japanese Patent Application No. 2007-519417.
European Search Report dated Dec. 3, 2009 issued in related European Patent Application No. 06735827.5.
European Office Action dated Jan. 11, 2010 issued in related European Patent Application No. 2005218302.
U.S. Office Action dated Jan. 25, 2010 issued in related U.S. Appl. No. 11/326,133.
International Search Report and Written Opinion dated Apr. 21, 2010 issued in related International Patent Application No. PCT/US2010/025095.
International Search Report and Written Opinion dated May 3, 2010 issued in related International Patent Application No. PCT/US2010/025464.

European Office Action dated Apr. 13, 2010 issued in related European Patent Application No. 02805182.9-2310.
European Office Action dated Mar. 25, 2010 issued in related European Patent Application No. 01997077.1-2310.
U.S. Office Action dated May 18, 2010 issued in related U.S. Appl. No. 12/415,503.
U.S. Office Action dated Sep. 2, 2009 issued in relation U.S. Appl. No. 10/994,453.
U.S. Office Action dated Oct. 5, 2009 issued in relation U.S. Appl. No. 10/789,545.
Japanese Notice of Reasons for Rejection dated Sep. 8, 2009 issued in related Japanese Patent Application No. 2003552147.
U.S. Office Action dated Oct. 14, 2009 issued in relation U.S. Appl. No. 11/461,240.
International Preliminary Report on Patentability dated Aug. 20, 2009 issued in related International Patent Application No. PCT/US2008/053194.
Australian Notice of Allowance dated Oct. 29, 2009 issued in related Australian Patent Application No. 2007216648.
Notice of Allowance dated Aug. 27, 2009 issued in related U.S. Appl. No. 10/760,965.
Notice of Allowance dated Oct. 9, 2009 issued in related U.S. Appl. No. 10/373,463.
Australian Office Action dated Oct. 29, 2009 issued in related Australian Patent Application No. 2007203623.
Notice of Allowance dated Aug. 25, 2009 issued in related U.S. Appl. No. 11/379,151.
International Search Report and Written Opinion dated Apr. 21, 2010 issued in related International Patent Application No. PCT/US2010/025095.
International Search Report and Written Opinion dated May 3, 2010 issued in related International Patent Application No. PCT/US2010/025464.
European Office Action dated Apr. 13, 2010 issued in related European Patent Application No. 02805182.9-2310.
European Office Action dated Mar. 25, 2010 issued in related European Patent Application No. 01997077.1-2310.
U.S. Office Action dated May 18, 2010 issued in related U.S. Appl. No. 12/415,503.
Office Action dated Sep. 2, 2010 issued in related U.S. Appl. No. 12/415,503.
Office Action dated Aug. 30, 2010 issued in related U.S. Appl. No. 12/397,095.
Australian Office Action dated Aug. 23, 2010 issued in related Australian Patent Application No. 2006203909.
Notice of Allowance dated Aug. 6, 2010 issued in related U.S. Appl. No. 11/359,892.
Canadian Office Action dated Jul. 29, 2010 issued in related Canadian Patent Application No. 2470936.
Habermeyer, Peter, ATOS News, Oct. 2005, "The Artificial Limb "Eclipse"—A new draft without shank in the implantation of artificial shoulder limbs", cover page w/pp. 40-41, with English translation dated Jan. 13, 2006 (2 pgs).
Thermann, et al, ATOS Newsletter, Jun. 2005, Aktuelle Therrien, (16 pages).
Gray, Henry, Anatomy of the Human Body, 1918, 6d. The Foot 1. The Tarsus, II. Osteology, cover page and 12 pgs, ww. Bartleby.com/107/63.html#i268 Oct. 25, 2004.
Chainsaw, Wikipedia, the free encyclopedia, http://en.wikipedia.org/w/index.php?title=Chainsaw&printable=yes, Jun. 26, 2007 (3 pages).
APTA | Knee,/http://www.apta.org/AM/PrinerTemplate.cfm?Section=Home&TEMPLATE=/CM/HTMLDisplay.dfg&... Jun. 25, 2007 (1page).
American Machinist, Full-radius milling cutters, http://www.americanmachinist.com/Classes/Article/ArticleDraw_P.aspx, Jun. 26, 2007 (1 page).
Chuck (engineering),Wikipedia, the free encyclopedia, http://en.wikipedia.org/w/index.php?title=Chuck_%28engineering%29&printable=yes, Jun. 25, 2007, (4 pages).
Dovetail Rails, http://www.siskiyou.com/MDRSeries.htm, Jun. 25, 2007 (2 pages).
Knee Resurfacing, Permedica, GKS, Global Knee System. Cod. 104570 vers 1.0 del Mar. 15, 2006 (8pages).
Makita Industrial Power Tools, Product Details Print Out, Chain Mortiser, http://www.makita.com/menu.php?pg=product_det_prn&tag=7104L, Jun. 26, 2007 (3pgs).
Milling machine, Wikipedia, the free encyclopedia, http://en.wikipedia.org/w/index.php?title=Milling_machine&printable=yes, Jun. 26, 2007 (4 pages).
Mortise and tenon, Wikipedia, the free encyclopedia, http://en.wikipedia.org/w/index.php?title=Mortise_and_tenon&printable=yes, Jun. 25, 2007 (3 pages).
Oka et al, "Development of artificial articular cartilage", Proc Instn Mech Engrs vol. 214 Part H, 2000 pp. 59-68 (10 pages).
M. Siguier, MD et al, "Preliminary Results of Partial Surface Replacement of the Femoral Head in Osteonecrosis", The Jorunal of Arthroplasty, vol. 14, No. 1, 1999, pp. 45-51.
T. Siguier, MD et al, Partial Resurfacing Arthroplasty of the Femoral Head in Avascular Necrosis, Clinical Orthopaedics and Related Research, No. 386, 2001, pp. 85-92.
Suganuma, et al—"Arthroscopically Assisted Treatment of Tibial Plateau Fractures", Arthroscopy: The Journal of Arthroscopic and Related Surgery, vol. 20, No. 10, Dec. 2004, pp. 1084-1089 (6 pages).
The Mini Uni: A New Solution for Arthritic Knew Pain and Disability, AORI, 4 pages, www.aori.org/uniknee.htm Apr. 20, 2004.
The Stone Clinic, Orthopaedic Surgery Sports Medicine and Rehabilitation, Unicompartmental Replacement (partial knee joint replacement), Aug. 21, 2000, 3 pages, www.stoneclinic.com/unicopartrepl.htm, Apr. 20, 2004.
Ushio et al, "Partial hemiarthroplasty for the treatment of osteonecrosis of the femoral hear", An Experimantal Study in the Dog, The Journal of Bone and Joint Surgery, vol. 85-B, No. 6, Aug. 2003, pp. 922-930 (9 pages).
Russell E. Windsor, MD, In-Depth Topic Reviews, Unicompartmental Knee Replacement, Nov. 7, 2002, 9 pages.
Yaw angle, Wikipedia, the free encyclopedia, http://en.wikipedia.org/w/index.php?title=Yaw_angle&printable=yes, Jun. 25, 2007 (1 page).
U.S. Office Action dated Oct. 15, 2010 received in related U.S. Appl. No. 12/027,121.
U.S. Supplemental Notice of Allowance dated Oct. 28, 2010 issued in related U.S. Appl. No. 12/415,503.
European Search Report dated Nov. 4, 2010 issued in related European Patent Application No. 07862736.1-1269.
Japanese Notice of Reasons for Rejection dated Jun. 1, 2010 issued in related Japanese Patent Application No. 2003394702.
European Office Action dated Jun. 1, 2010 issued in related European Patent Application No. 04811836.8-2310.
Japanese Notice of Reasons for Rejection dated Jun. 29, 2010 issued in related Japanese Patent Application No. 2007519417.
Australian Office Action dated Jun. 11, 2010 issued in related Australian Patent Application No. 2005277078.
International Search Report dated Jun. 9, 2010 issued in related International Patent Application No. PCT/US2010/031594.
European Office Action dated May 7, 2010 issued in related European Patent Application No. 06733631.3-2310.
International Search Report dated Jun. 18, 2010 issued in related International Patent Application No. PCT/US2010/031602.
U.S. Office Action dated Jun. 8, 2010 issued in related U.S. Appl. No. 11/209,170.
Notice of Allowance dated Nov. 26, 2010 issued in related U.S. Appl. No. 11/209,170.
Supplemental Notice of Allowance dated Dec. 8, 2010 issued in related U.S. Appl. No. 11/209,170.
Notice of Allowance dated Dec. 13, 2010 issued in related U.S. Appl. No. 12/397,095.
Notice of Allowance dated Sep. 9, 2010 issued in related U.S. Appl. No. 10/994,453.
Office Action dated Sep. 21, 2010 issued in related U.S. Appl. No. 11/169,326.
Office Action dated Sep. 29, 2010 issued in related U.S. Appl. No. 11/461,240.
Office Action dated Oct. 11, 2010 issued in related Australian Patent Application No. 2006216725.

International Preliminary Report on Patentability dated Sep. 16, 2010 issued in related International Patent Application No. PCT/US2009/035889.
Supplemental Notice of Allowance dated Oct. 13, 2010 issued in related U.S. Appl. No. 10/994,453.

Supplemental Notice of Allowance dated Oct. 6, 2010 issued in related U.S. Appl. No. 12/415,503.

* cited by examiner

US 7,951,163 B2

RETROGRADE EXCISION SYSTEM AND APPARATUS

CROSS-REFERENCE TO RELATED APPLICATIONS

This application is a continuation-in-part of U.S. patent application Ser. No. 11/326,133, filed on Jan. 5, 2006, which claims the Benefit of U.S. provisional patent application Ser. No. 60/641,552, filed Jan. 5, 2005, and which is itself a continuation-in-part of U.S. patent application Ser. No. 11/209,170, filed Aug. 22, 2005, which claims the benefit of U.S. provisional patent application Ser. No. 60/603,473, filed Aug. 20, 2004, which is a continuation-in-part of U.S. patent application Ser. No. 11/169,326, filed Jun. 28, 2005, which claims the benefit of U.S. provisional patent application Ser. No. 60/583,549, filed Jun. 28, 2004, which is a continuation-in-part of U.S. patent application Ser. No. 10/994,453, filed Nov. 22, 2004, which claims the benefit of U.S. provisional patent application Ser. No. 60/523,810, filed Nov. 20, 2003. Each of the above-listed applications is incorporated herein by reference in their entirety.

FIELD

The present disclosure relates to a system and apparatus for excising an articular surface, and more particularly relates to a cutter system and method of use.

BACKGROUND

Articular cartilage, found at the ends of articulating bone in the body, is typically composed of hyaline cartilage, which has many unique properties that allow it to function effectively as a smooth and lubricious load-bearing surface. However, when injured, hyaline cartilage cells are not typically replaced by new hyaline cartilage cells. Healing is dependent upon the occurrence of bleeding from the underlying bone and formation of scar or reparative cartilage called fibrocartilage. While similar, fibrocartilage does not possess the same unique aspects of native hyaline cartilage and tends to be far less durable.

Hyaline cartilage problems, particularly in knee and hip joints, are generally caused by disease such as occurs with rheumatoid arthritis or wear and tear (osteoarthritis). Hyaline cartilage problems may also be the result of an injury, either acute (sudden) or recurrent and chronic (ongoing). Such cartilage disease or deterioration can compromise the articular surface causing pain and further deterioration of joint function. As a result, various methods have been developed to treat and repair damaged or destroyed articular cartilage.

BRIEF DESCRIPTION OF DRAWINGS

Features and advantages of the present invention are set forth by description of embodiments consistent therewith, which description should be considered in conjunction with the accompanying drawings, wherein.

DESCRIPTION

Figure 1:
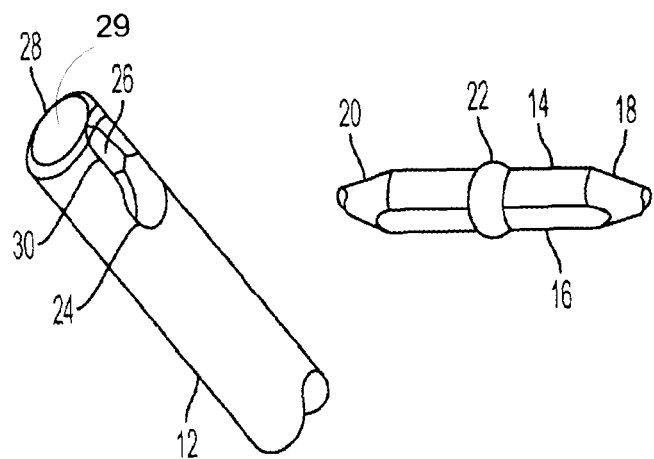
FIG. 1 is a perspective view of a portion of an excision tool consistent with the present disclosure in an uncoupled condition.
Figure 2:
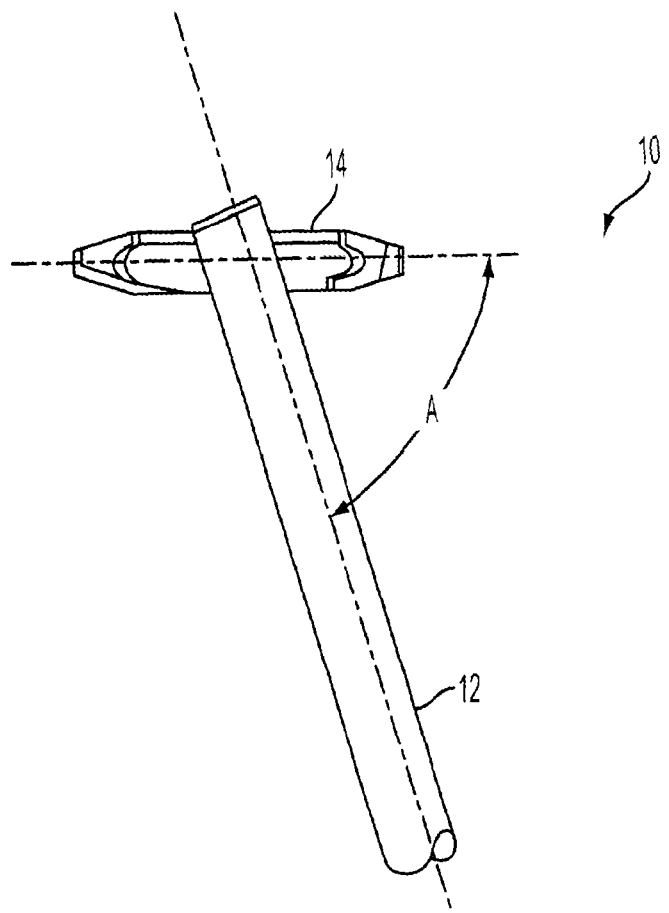
FIG. 2 is a side elevation view of a portion of the excision tool shown in FIG. 1 in a coupled condition.

Referring to FIGS. 1 and 2, an embodiment of an excision tool 10 is shown. Generally, the excision tool 10 may include a central shaft 10 and a cutter 14. According to one aspect, the central shaft 12 and the cutter 14 may be configured to allow the cutter 14 to be coupled to the central shaft 12 in such a manner that the cutter 14 may be rotated by the central shaft 12. In addition to being coupled to permit the cutter 14 to be rotated by the central shaft 12, the cutter 14 may be coupled to the central shaft 12 in a manner to permit the cutter 14 to tilt and/or assume an angular relationship relative to the central shaft 12. The cutter 14 may be configured to allow the cutter to tilt relative to the central shaft 12 during rotation of the cutter 14 by the central shaft 12.

Consistent with the illustrated excision tool 10, the central shaft 12 may be configured as a longitudinal member. For example, the central shaft 12 may be configured as a generally cylindrical rod. The cutter 14 may also generally be provided as a longitudinal member having at least one cutting and/or scraping edge 16. Consistent with the illustrated embodiment, the cutter 14 may be provided having tapered ends 18, 20.

In the illustrated embodiment, the cutter 14 may include a ball 22 or rounded featured disposed between the ends 18, 20 of the cutter 14. The ball 22 may be sized to be received in an opening 24 in the central shaft 12. The central shaft 12 may include an internal passage 26 extending from the opening 24. The internal passage 26 may extend toward an end 28 of the central shaft 12, as shown, in an embodiment configured for retrograde application. According to such a configuration, the cutter 14 may be inserted through the opening 24 in the central shaft 12 to position the ball 22 generally within the central shaft 12. The cutter 14 may then be translated toward the end 28 of the central shaft 12, engaging the ball 22 in the internal passage 26 of the central shaft 12 and engaging the cutter 14 in a slot 30 through the central shaft 12 extending from the opening 24.

In a related embodiment, which may be suitable for use in an end-on application, the internal passage and the slot through the central shaft may extend away from the end of the central shaft. In such an embodiment, the cutter may be inserted through the opening in the central shaft and translated away from the end of the central shaft. Similar to the illustrated embodiment, translation of the cutter relative to the central shaft may engage the ball in the internal passage of the central shaft and engage the cutter in the slot of the central shaft.

As shown in FIG. 2, when the ball 22 is engaged in the internal passage 26 and the cutter 14 is received through the slot 30, the cutter 14 may tilt relative to the axis of the central shaft 12. Accordingly, the cutter 14 may achieve a tilt angle A relative to the central shaft 12. The angular range of movement achievable by the cutter 14 relative to the central shaft 12 may be a function of a variety of design considerations, such as ball diameter, cutter size, relief features in the cutter and/or the central shaft, etc. Additionally, when the ball 22 is engaged in the internal passage 26 of the central shaft 12, the cutter may resist separation from the central shaft 12.

In an embodiment, the internal passage 26 of the central shaft may be formed by providing a hole extending from the opening 24 toward the end 28 of the central shaft 12, with the hole being sized to receive the ball 22 in order to permit the ball 22, and cutter 14 therewith, to translate toward the end 28 of the central shaft. In one such embodiment, the hole may be formed by drilling inwardly from the end 28 of the central shaft 12 toward the opening 24. The hole may then be closed adjacent the end 28 of the central shaft, as with a plug, end cap, etc., 29.

Consistent with the illustrated embodiment, the cutter 14 may be releasably coupled to the central shaft 12. Additionally, while the interaction of the ball 22 and the internal passage may allow the cutter 14 to tilt relative to the central shaft 12, the interaction of the cutter 14 and the slot 30 may restrict independent rotation of the cutter 14 about the axis of the central shaft 12. As such, the cutter 14 may be rotated about the axis of the central shaft 12 by rotating the central shaft 12.

In general, the excision tool according to the present disclosure may include a cutter that may be rotated and that may tilt relative to the axis of rotation. As in the illustrated embodiment, the cutter may be coupled to a shaft which may rotate the cutter. The cutter may tilt relative to the axis of rotation, i.e., relative to the axis of the shaft which may rotate the cutter. Desirably, the cutter may be configured so that the angle of the cutter relative to the axis of rotation may vary and/or be varied while the cutter is being rotated. Furthermore, consistent with the present disclosure, the angle of the cutter relative to the axis of shaft may vary and/or be varied during each revolution of the cutter. Accordingly, the cutter may be pivotally coupled relative to the shaft and may be generally torsionally rigid relative to the shaft.

Referring to FIGS. 3 through 7, an excision tool consistent with the present disclosure may be employed to create an excision site in an articular surface 100 of a joint, and/or in the bone underlying the articular surface. For the convenience of description, as used herein an excision site in an articular surface contemplates an excision site created by the removal of at least a portion of an articular surface and may further contemplate the removal of bone underlying the articular surface. According to various embodiments, an excision site created using an excision tool consistent with the present disclosure may be employed for a variety of purposes. For example, the excision site may be created to remove a damaged and/or diseased portion of an articular surface. Additionally and/or alternatively an excision site may be created to provide an implant site for replacing at least a portion of the articular surface 100.

According to one aspect, an excision tool consistent with the present disclosure may be used in connection with a retrograde access procedure to provide an excision site in the articular surface from an access point behind the articular surface. Generally, a retrograde procedure may include locating a portion of an articular surface that is to be excised. An access tunnel may be formed in a bone behind the articular surface and the access tunnel may extend toward the articular surface. According to various embodiments, such a retrograde procedure may include providing an axis extending through the bone and the portion of the articular surface to be excised. The access tunnel may be drilled through the bone along the axis and toward the articular surface. In some embodiments, a stop sheath may be installed in the bone behind the articular surface. The stop sheath may include a threaded member having a passage therethrough. The stop sheath may be threadably engaged with the bone, allowing the stop shaft to be screwed into, and out of, the bone, respectively toward and away from the articular surface. The passage through the stop sheath may provide a passage toward the articular surface and may define an axis relative to the articular surface. Additionally, in some embodiments, the passage of the stop sheath may be employed as a bushing, e.g., for supporting rotating tools extending through the passage. Examples of suitable retrograde procedures are generally described in U.S. patent application Ser. No. 11/169,326, filed Jun. 28, 2005, and U.S. patent application Ser. No. 10/994,453, filed Nov. 22, 2004, and U.S. patent application Ser. No. 60/641,552, filed Jan. 5, 2005, the entire disclosures of all of which are incorporated herein by reference.

Figure 3:
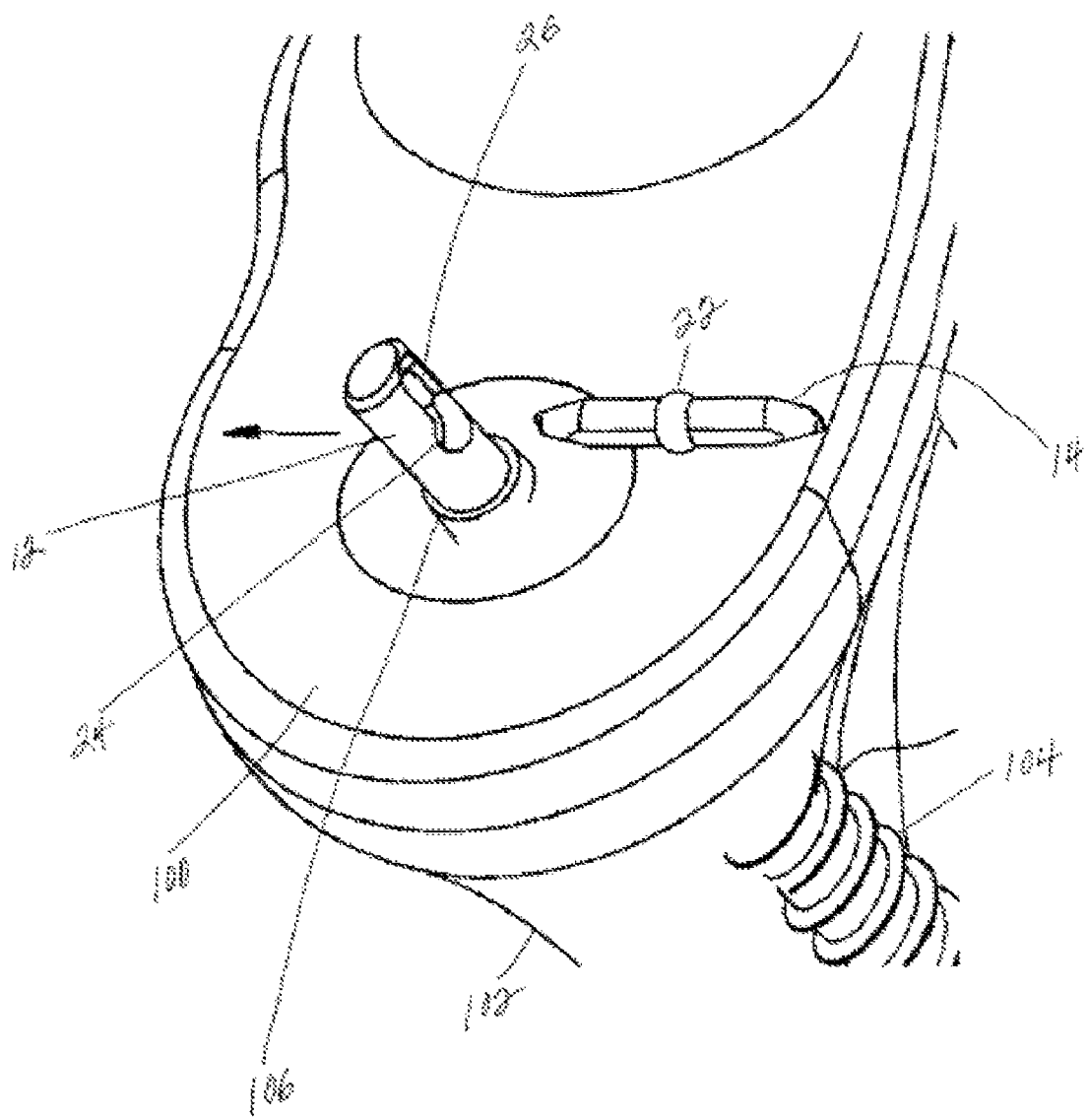
FIG. 3 is a perspective view showing the implementation of an embodiment of an excision system consistent with the present disclosure.

Referring to FIG. 3, a stop sheath 104 is shown installed in a bone 102 with a distal end 106 of the stop sheath 104 generally tangential and/or flush with the articular surface 100. Consistent with the present disclosure, the stop sheath 104 may be installed at various heights relative to the articular surface, including protruding above and/or recessed below the articular surface 100, as well as flush with the articular surface 100, as shown. Positioning of the distal end 106 of the stop sheath 104 relative to the articular surface 100 may include visual inspection of the stop sheath 104 relative to the articular surface 100. Additionally, and/or alternatively, the position of the stop sheath 104 may be evaluated using a variety of test equipment, including feelers, radiographic imaging, etc.

Figure 4:
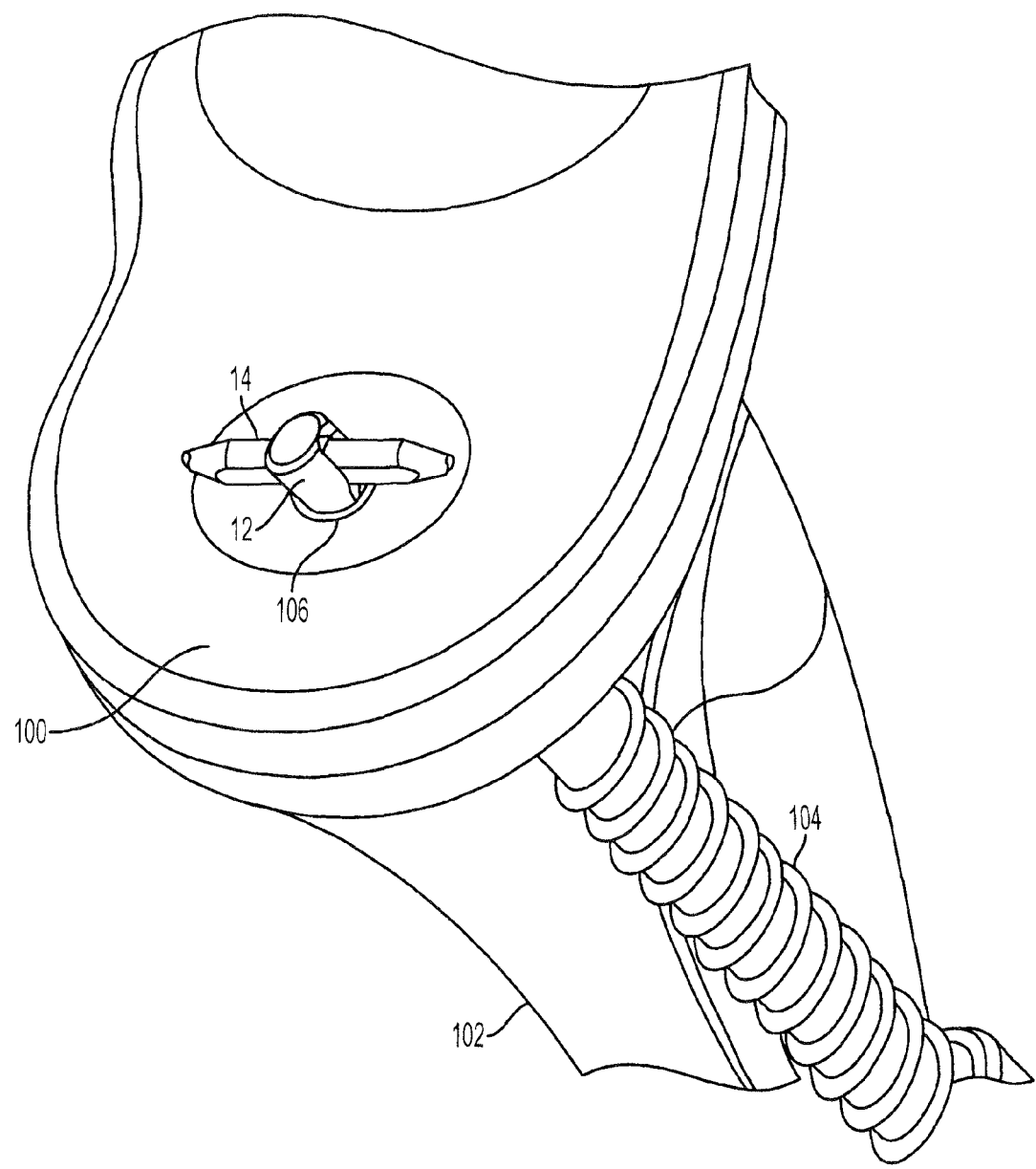
FIG. 4 is a perspective view of an embodiment of an excision system consistent with the present disclosure disposed to excise a portion of an articular surface.
Figure 6:
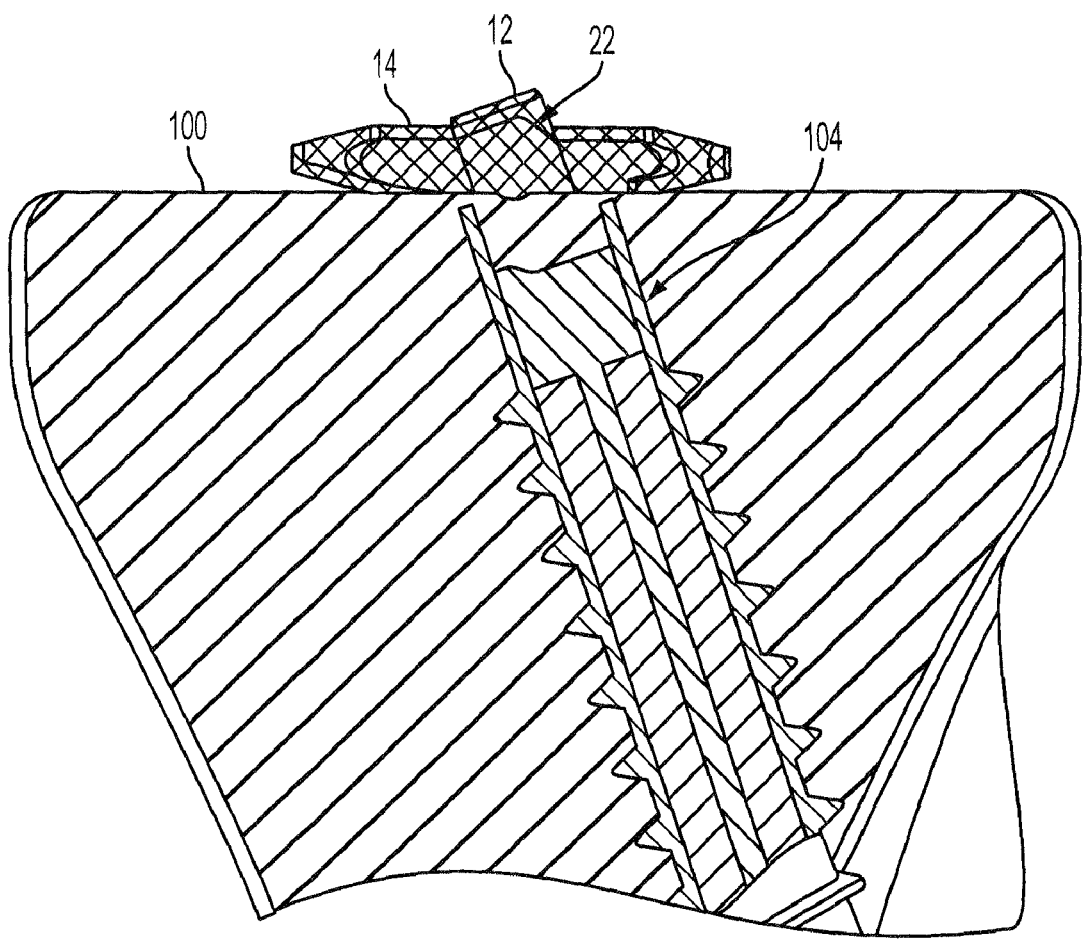
FIG. 6 is a cross-sectional view of an embodiment of an excision system consistent with the present disclosure disposed to excise a portion of an articular surface.

The central shaft 12 of the excision tool may be inserted at least partially through the stop sheath 104, e.g., to expose at least a portion of the opening 24 of the central shaft 12 above the distal end 106 of the stop sheath 104. As indicated by the arrow, with at least a portion of the opening 24 exposed above the stop sheath 104, the cutter 14 may be inserted into the opening 24 and the ball 22 of the cutter 14 may be engaged in the slot 26 of the central shaft 12, e.g., by moving the cutter 14 distally relative to the central shaft 12 and/or by withdrawing the central shaft 12 away from the articular surface 100. Consistent with the foregoing, the central shaft 12 and cutter 14 may be coupled to one another to provide the assembled excision tool 10 with the cutter 14 positioned on, and/or adjacent to, the articular surface 100, as shown in FIGS. 4 and 6.

Figure 5:
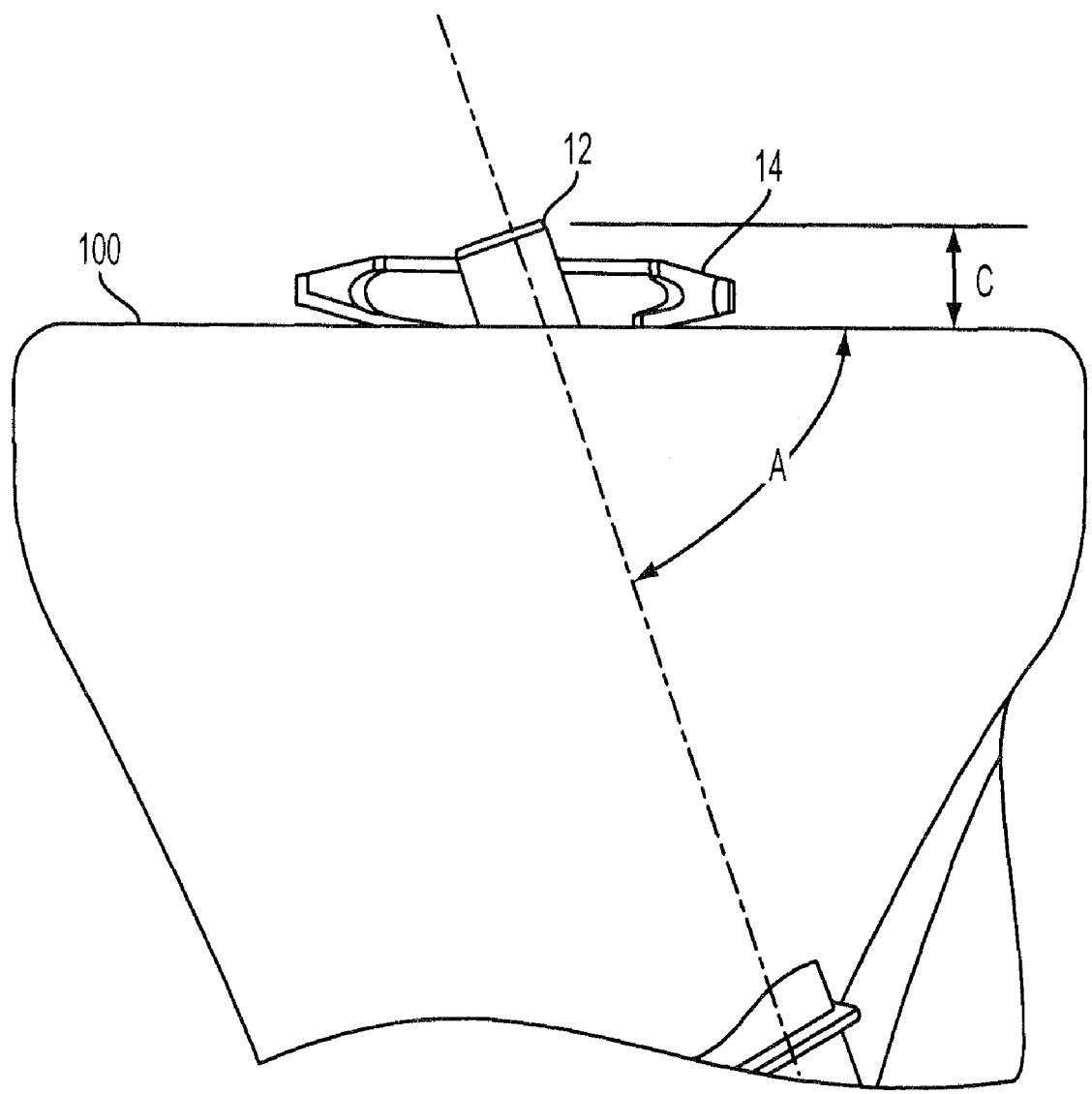
FIG. 5 is a side elevation view of the excision system depicted in FIG. 4 showing an orientation of the excision system.

Referring to FIG. 5, consistent with the present disclosure, the cutter 14 may be coupled to the central shaft 12 within a relatively small clearance above the articular surface 100. For example, according to one embodiment, the central shaft 12 and the cutter 14 may be coupled to one another within a clearance C in a range of about 4-5 mm above the articular surface 100. The relatively small clearance C above the articular surface 100 required for assembling the central shaft 12 and the cutter 14 may allow an excision tool consistent with the present disclosure to be used to create an excision site in the articular surface without dislocating the joint including the articular surface 100 and, thereby, avoiding the associated trauma of a dislocation of the joint. In this manner, according to one aspect, an excision tool consistent with the present disclosure may not only allow an excision of the articular surface without requiring direct access to the face of the articular surface, but may additionally minimize the invasiveness of the procedure by requiring minimal separation between the articular surface and adjacent features. According to alternative embodiments, however, greater clearances between the articular surface and surrounding features may be employed. Such alternative embodiments may include the dislocation and/or separation of a joint including the articular surface.

Figure 7:
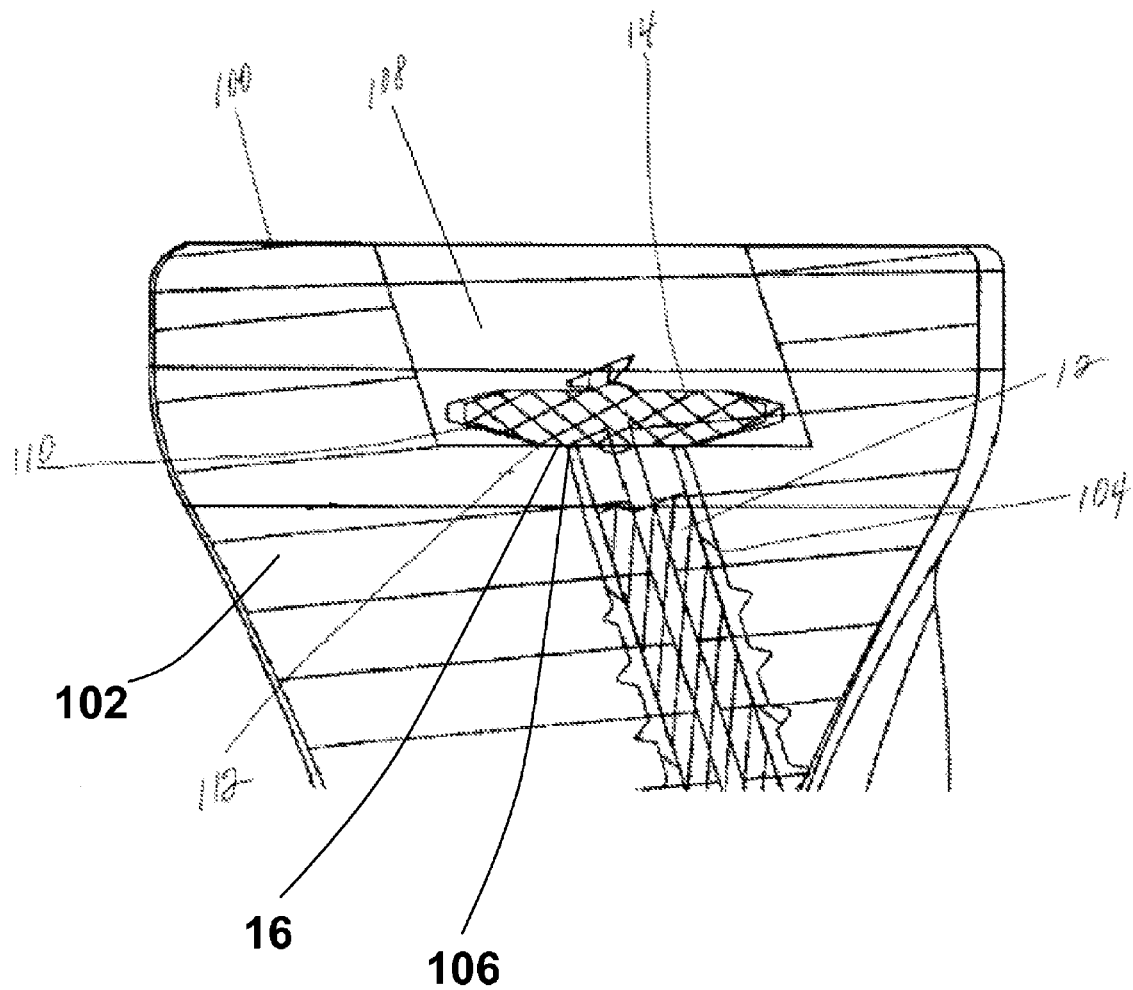
FIG. 7 is a cross-sectional view of an embodiment of an excision system consistent with the present disclosure after excising a portion of an articular surface.

Turning to FIG. 7, with the central shaft 12 and the cutter 14 assembled to one another, an excision site 108 may be created extending inwardly from the articular surface 100. The excision site 108 may be created by rotating the cutter 14, e.g., by rotationally driving the central shaft 12, and applying a retrograde force to the cutter 14. The central shaft 12 may be rotationally driven either manually or using a drive motor, such a as a drill. As discussed above, the interaction of the cutter 14 and the central shaft 12 may allow the cutter 14 to be rotated by rotationally driving the central shaft 12. In an embodiment utilizing a stop sheath 104, the central shaft 12 may be rotated within the stop sheath 104. In such an embodiment, the stop sheath 104 may function as a bushing and guide the rotation of the central shaft 102. In alternative embodiments, the central shaft may be disposed in the access tunnel through the bone without the use of a stop sheath. Consistent with such an embodiment, rotation of the central shaft may be guided by the access tunnel and/or by the orientation of the drive motor, etc.

The retrograde force applied to the cutter 14 may urge the cutter 14 into the articular surface 100. As the cutter 14 is urged into the articular surface 100, the cutting and/or scraping edge 16 of the cutter 14 may engaged the articular surface 100 and may excise at least a portion of the articular surface 100, thereby creating an excision site 106. As depicted, the excision site 108 created as the cutter is urged into the articular surface may generally correspond to a projection of the rotating cutter along the path of the applied retrograde force.

Consistent with one embodiment, a retrograde force may be applied to the cutter 14 by withdrawing the stop sheath 104 in the access tunnel. According to such an embodiment, the axial position of the central shaft 12 relative to and/or within the stop sheath 104 may be maintained as the stop sheath 104 is withdrawn away from the articular surface 100. For example, the central shaft may be provided with a collar or other suitable mechanism to allow the central shaft to be withdrawn away from the articular surface along with the stop sheath. Accordingly, a retrograde force applied to the stop sheath 104 may be transmitted to the cutter 14 through the central shaft 12.

In an embodiment in which the stop sheath 104 is threadably engaged with the bone 102 defining the access tunnel, the stop sheath 104 may be withdrawn away from the articular surface 100, by threadably withdrawing the stop sheath 104 away from the articular surface 100. That is, the stop sheath 104 may be unscrewed from the bone 102. With the axial position of the central shaft 12 maintained generally constant relative to the stop sheath 104, as the stop sheath 104 is threadably withdrawn away form the articular surface 100, the central shaft 12 may similarly be withdrawn away from the articular surface 100, thereby applying a retrograde force to the cutter 14. As discussed above, the retrograde force applied to the cutter 14 may urge the cutting and/or scraping edge 16 of the cutter to excise at least a portion of the articular surface 100.

The depth of the excision site may be controlled by controlling the distance the cutter is moved into the articular surface. In the foregoing embodiment, in which the cutter is urged into the articular surface by threadably withdrawing the stop sheath and the central shaft away from the articular surface, the depth of the excision site may be controlled by controlling the distance the stop sheath is withdrawn away from the articular surface. According to one embodiment, the distance that the stop sheath is withdrawn away from the articular surface may be directly measured, e.g., using reference marks on the stop sheath, etc. According to another embodiment, the depth of the excision site may be controlled based on the number of revolutions the stop sheath is threadably withdrawn. For a given thread pitch of the stop sheath, the distance the stop sheath is withdrawn, and therefore the distance the cutter is drawn into the articular surface, may be related to the thread pitch and the number of revolutions through which the stop sheath rotated. Accordingly, the depth of the excision site may be controlled by controlling the number of revolutions over which the stop sheath is withdrawn corresponding to a distance of axial travel based on the thread pitch of the stop sheath.

According to additional and/or alternative embodiments, the stop sheath may initially be provided with the distal end of the stop sheath recessed below the articular surface. In such an embodiment, the retrograde force may be applied to the cutter by withdrawing the central shaft away from the articular surface. The retrograde force applied to central shaft may be transmitted to the cutter coupled thereto. Similar to the manner described above, the retrograde force applied to the cutter may urge the cutter into the articular surface, thereby urging the cutting or scraping edge of the cutter into the articular surface and excising at least a portion of the articular surface.

Consistent with the foregoing embodiment, the stop sheath may be moved to a position beneath the articular surface. The central shaft may be withdrawn relative to the articular surface urging the cutter into the articular surface to form an excision site therein. According to an embodiment, the cutter may be urged into the articular surface until a portion of the cutter bears against and/or contacts at least a portion of the stop sheath. As shown, for example in FIG. 7, the cutter 14 may include a bearing surface 112 which may contact the distal end 106 of the stop sheath 104 and provide little or no abrading of the cutter 14 and/or stop sheath 104, thereby resulting in the release of little or no attendant particulate material. Accordingly, the depth of the excision site may be controlled by the depth of the stop sheath below the articular surface.

According to one such embodiment, the stop sheath can be placed at a depth below the articular surface to provide a desired excision site depth. Depth of the stop sheath may be set by measuring a height of a distal end of the stop sheath relative to the articular surface. According to another embodiment, the stop sheath may first be set at a height relative to the articular surface, for example, the distal end of the stop sheath may be set generally tangential to the articular surface. The stop sheath may then be threadably withdrawn away from the articular surface to a desired depth below the articular surface. Withdrawal of the stop sheath away from the articular surface may be based on a known thread pitch of the stop sheath and the number of revolutions turned during withdrawal, thereby generally giving a known distance of axial travel of the stop sheath relative to the articular surface. The cutter may then be drawn down into the articular surface to contact the stop sheath, thereby providing an excision site depth generally controlled by the depth of the stop sheath.

According to another embodiment, the excision site may be produced by withdrawing the central shaft, with the cutter coupled to the central shaft, relative to the articular surface. The depth of the excision site may be controlled with reference to the withdrawal of the central shaft. The withdrawal of the central shaft may be determined based on direct measurement, measurement relative to another instrument, using marking or indicia on the central shaft, etc. In yet another embodiment, the excision site may be formed by urging the cutter into the articular surface, and controlling the depth of the excision site relative to a measured and/or observed depth of the cutter.

As discussed previously, the cutter 14 may be coupled to the central shaft 12 to permit the cutter to tilt or pivot relative to the central shaft 12. Consistent with the present disclosure, tilting movement of the cutter 14 relative to the central shaft 12 may occur during rotation of the cutter 14 by the central shaft 12. The cutter 14 may, therefore, rotate on a plane that is not perpendicular to the axis of the central shaft 12. As such, the cutter 14 may rotate in a plane that is not perpendicular to the axis of rotation of the cutter. Similarly, when the retrograde force is applied to the cutter 14 through the central shaft 12, the cutter 14 may rotate in a plane that is at an angle to, i.e., that is not perpendicular to, the direction of the retrograde force. Rotation of the cutter 14 in a plane that is not perpendicular to the axis of the retrograde force may allow the cutter 14 to create an excision site having a bottom 110 that is also not perpendicular to the axis of the retrograde force, and not perpendicular to the axis of the central shaft.

Consistent with the embodiment depicted in FIGS. 3 through 6, the stop sheath 104 may initially be positioned adjacent to the articular surface 100. That is, prior to and/or as excision begins, the stop sheath 104 may be disposed adjacent to the articular surface 100. As shown, for example in FIG. 7, the cutter 14 may include a bearing surface 112 which may contact and/or be disposed proximate to the distal end 106 of the stop sheath 104. Accordingly, as the cutter 14 is rotated, the bearing surface 112 of the cutter 14 may follow the surface of the distal end 106 of the stop sheath 104. The orientation of the cutter 14 may vary according to the profile of the distal end 106. In such an embodiment, the orientation of the cutter 14 may be controlled by the geometry of the distal end 106 of the stop sheath 104. In the depicted embodiment, the cutter 14 may exhibit a constant angular relationship relative to the axis of the stop sheath 104 and central shaft 12 through each rotational cycle of the cutter 14. In further embodiments, it is contemplated that the orientation of the cutter may vary throughout each rotational cycle.

As a retrograde force is applied to the cutter 14, and the cutter 14 is drawn into the articular surface, the orientation of the cutter 14 may be controlled by, and/or may be a function of, the geometry of the distal end 106 of the stop sheath 104. As the stop sheath 104 is withdrawn away from the articular surface 100, with a bearing surface 112 of the cutter 14 being maintained in contact with the distal end 106 of the stop sheath 104, the resulting excision site 108 may have a shape corresponding to the intersection of the rotating cutter, oriented according to the geometry of the distal end 106 of the stop sheath 104, and the articular surface projected along the axis of the retrograde force. For example, if the cutter is maintained generally parallel to the articular surface, the intersection of the rotating cutter and the articular surface may provide an excision site having a circular cross-section that may be projected into the articular surface at an angle relative to the articular surface corresponding to the angle of the retrograde force. As shown in FIG. 7, the excision site 108 may have a circular cross-section parallel to the articular surface and may slope inwardly from the articular surface. Additionally, the excision site may have a bottom 110 that may be generally parallel to the articular surface, although the bottom surface or the articular surface may correspond to the bottom geometry of the cutter. In an embodiment in which the plane of rotation of the cutter is at an angle relative to the articular surface, the excision site may having an elliptical cross-section parallel to the articular surface and may be projected into the articular surface along the axis of the applied retrograde force.

In a related embodiment, a sleeve may be disposed at least partially within the stop sheath and the central shaft may extend through the sleeve. The sleeve may be positioned so that the distal end of the sleeve may extend beyond the distal end of the stop sheath. Furthermore, the distal end of the sleeve may be configured and/or positioned to contact and/or be disposed adjacent to the bearing surface of the cutter. As the cutter is rotated by the central shaft, the orientation of the cutter may be controlled and/or guided by the distal end of the sleeve. In one embodiment, the central shaft and/or the stop sheath may be rotated independently of the sleeve. The axial position of the central shaft may be maintained generally constant relative to the stop sheath during an excision operation. A retrograde force may be applied to the cutter by threadably withdrawing the stop sheath, and the central shaft therewith, away form the articular surface. The sleeve may remain rotationally independent of the central shaft, which may rotationally drive the cutter, and of the stop sheath, which may rotate to threadably withdraw the stop sheath and central shaft. In this manner, according to one embodiment the cutter may be rotated and the stop sheath may be threadably withdrawn without rotating the sleeve. That is, the sleeve may be kept from rotating, while the central shaft and the stop sheath are being rotated. The sleeve may, however, be maintained in a generally axial relationship relative to the cutter, the central shaft, and the stop sheath. The sleeve may, therefore, be axially withdrawn away from the articular surface along with the stop sheath, the central shaft, and the cutter.

The distal end of the sleeve may be maintained in contact with and/or proximate to the bearing surface of the cutter as the cutter, the stop sheath, and the central shaft, along with the sleeve, are withdrawn away form the articular surface. In such an embodiment, the orientation of the cutter may be controlled by and/or related to the geometry of the distal end of the sleeve. Because the sleeve does not rotated as it is withdrawn, the orientation and/or pattern of orientation of the cutter may be maintained generally constant as the articular surface is excised. For example, the distal end of the sleeve may be angled relative to the axis of the sleeve, and may similarly be angled relative to the axis of the central shaft, for example, other than being perpendicular to the axis of the central shaft. Accordingly, the cutter may be oriented at an angle corresponding to the sleeve, which may be an angle other than perpendicular to the axis of the central shaft and the stop sheath. The cutter may, therefore, be oriented at an angle relative to a retrograde force which may be applied by the stop sheath and/or the central shaft. When the sleeve is maintained in a rotationally fixed relationship, e.g., relative to the articular surface, as the sleeve, the stop sheath, the central shaft, and the cutter are all withdrawn away from the articular surface, the angle or plane defined by the distal end of the sleeve may remain constant, e.g., relative to the articular surface. Accordingly, the orientation, and/or pattern of orientation, of the cutter may remain constant, e.g., relative to the articular surface, as the cutter is drawn into the articular surface to create an excision site.

As alluded to above, the distal end of the sleeve may have a varying profile around the circumference of the sleeve. As the cutter is rotated with the bearing surface of the cutter in contact with and/or adjacent to the varying profile of the distal end of the sleeve, the orientation of the cutter may vary about each rotational cycle. As the cutter is rotated with the bearing surface of the cutter in contact with the distal end of the sleeve, the orientation of the cutter may be controlled by and/or guided by the profile of the distal end of the sleeve. Variation in the orientation of the cutter about each rotational cycle may provide an intersection of the rotating cutter and the articular surface producing an excision site having a cross-sectional shape other than circular or elliptical.

According to an alternative embodiment, the distal end of the stop sheath may, at least initially, be spaced from the cutter. In such an embodiment, the bottom edge of the cutter, i.e., the cutting or scraping edge, may generally follow the profile of the articular surface as the cutter is drawn into the articular surface. Accordingly, as the cutter is rotated in contact with the articular surface, the orientation of the cutter may generally be controlled by and/or be a guided by the geometry of the articular surface. Depending upon the geometry of the articular surface, the orientation of the cutter may remain generally constant throughout each rotational cycle. In such an embodiment, the intersection of the rotating cutter and the articular surface may produce an excision site having a generally uniform and/or symmetrical cross-sectional shape.

Alternatively, if the geometry of the articular surface is not locally uniform in the area of contact between the cutter and the articular surface, the orientation of the cutter may vary about the rotation of the cutter, i.e., throughout each rotational cycle of the cutter. The change in the orientation of the cutter throughout each rotational cycle may generally be based on the geometry of the articular surface contacted by the bottom edge of the cutter, i.e., the cutting or scraping edge. An initial excision site may be created having a cross-sectional geometry generally parallel to a plane of the articular surface defined by the intersection of the rotating cutter and the articular surface. The geometry of the excision site formed after the initial excision of the articular surface may be generally constant if the cutter transfers the varying geometry of the articular surface to the bottom of the excision site being formed. Alternatively, the bottom of the excision site may become uniform and/or continue to vary as the depth of the excision site increases.

Consistent with either of the foregoing embodiments in which the orientation of the cutter is controlled and/or guided by the geometry of the articular surface contacted by the bottom edge of the cutter, the bottom of the excision site may be controlled by a stop sheath. For example, a stop sheath may be at least partially disposed within an access tunnel extending into a bone beneath the articular surface and extending toward the articular surface. The distal end of the stop sheath may be disposed beneath the articular surface. The cutter may be rotated in contact with the articular surface and a retrograde force may be applied to urging the cutter into the articular surface to form an excision site. The cutter may be drawn into the articular surface until a portion of the cutter contacts the stop sheath. The cutter may further be urged toward the stop sheath and may continue to excise the articular surface and/or underlying bone until a portion of the bottom surface, e.g., a bearing surface, of the cutter contacts the distal end of the stop sheath about the entire rotation of the cutter. When the bottom of the cutter contacts the distal end of the stop sheath through the entire rotation of the cutter, the orientation of the cutter may generally be controlled and/or guided by the geometry of the distal end of the stop sheath. Similarly, the bottom of the excision site may be controlled by the geometry of the distal end of the stop sheath.

According to yet another variation on the preceding embodiments, an excision site may be created using an excision tool herein without the use of a stop sheath. According to such an embodiment, the orientation of the cutter may be controlled and/or guided by the geometry of the articular surface contacted by the rotating cutter. The central shaft rotating the cutter and applying a retrograde force to the cutter may be disposed extending at least partially through an access tunnel in the bone underlying the articular surface. The bone defining the access tunnel may act as a bushing supporting the rotating central shaft. Accordingly, the rotating shaft and the axis of the retrograde force applied to the cutter may generally be controlled and/or guided by the access tunnel. The depth of the excision site may generally be controlled according to a measured and/or observed distance the central shaft is withdrawn and/or by reference to a measured and/or observed depth of excision or position of the cutter. The cross-sectional geometry of the excision site relative to a plane generally parallel to the articular surface may be based on the orientation of the cutter throughout the rotation of the cutter as controlled by the interaction of the articular surface and the bottom edge of the cutter.

Figure 8:
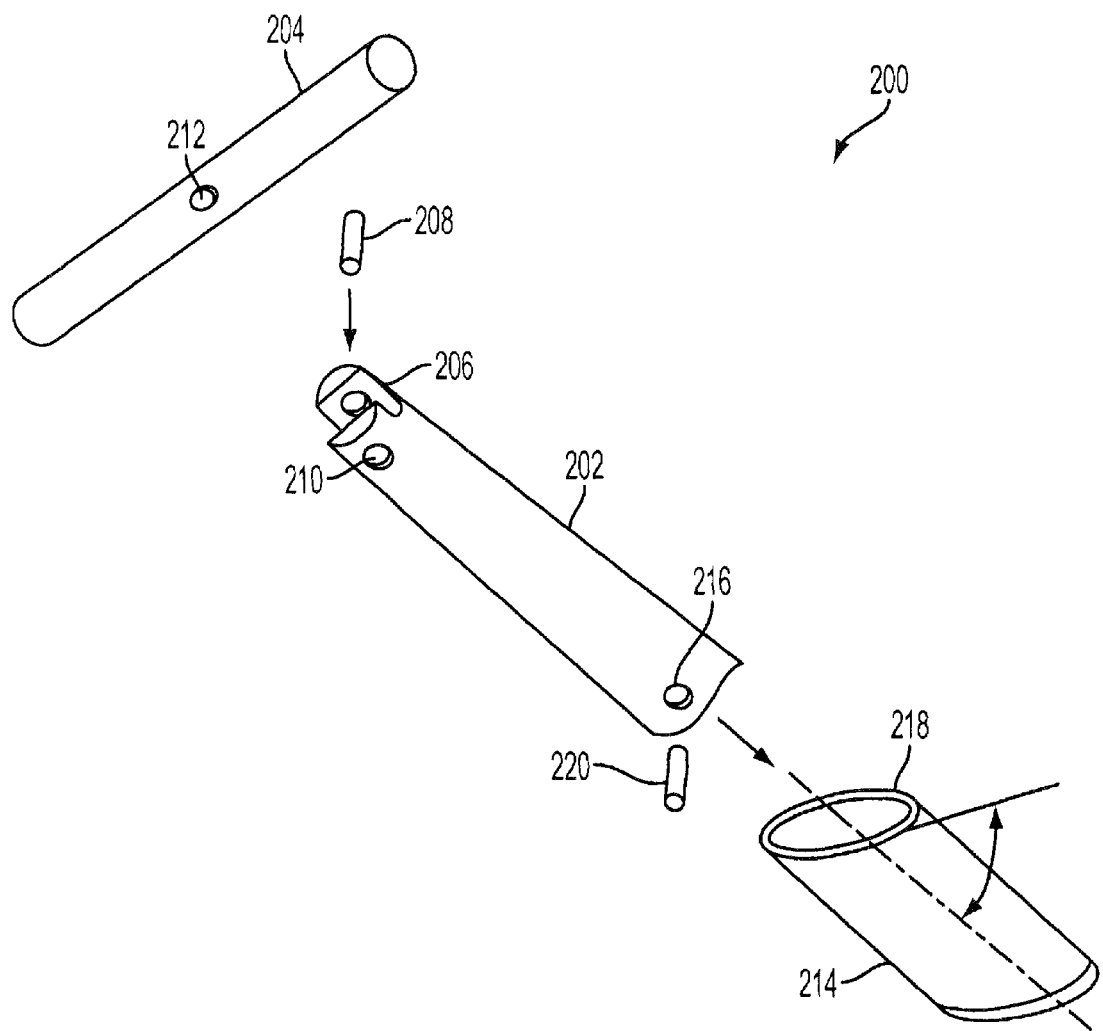
FIG. 8 is an exploded view of another embodiment of an excision tool consistent with the present disclosure.

Turning to FIG. 8, a partial exploded view of another embodiment of an excision tool 200 is depicted. The excision tool 200 may generally include a shaft 202 and a cutter 204 which may be removably coupled to the shaft 202. As shown, the cutter 204 may be configured to be at least partially received in a notch 206 in the distal end of the shaft 202. Furthermore, the cutter 204 may be removably coupled to the shaft 202 by a pin 208, which may extend through corresponding openings 210, 212 in the shaft 202 and the cutter 204. According to one aspect, the pin 208 may pivotally couple the cutter 204 to the shaft 202. The cutter 204 may be capable of tilting or pivoting relative to the shaft 202 and may achieve various angular orientations to the shaft 202.

The shaft 202 of the excision tool 200 may be configured to be at least partially received in a stop sheath 214. The shaft 202 may be rotatably and/or slidably received in the stop sheath 214. The stop sheath 214 may be capable of being engaged in bone behind an articular surface. In one embodiment, the shaft 202 may extend through the stop sheath 214 and the stop sheath 214 may operate as a bushing for rotatably and/or slidably supporting the shaft 202. The shaft 202 may include a hole 216 adjacent to a distal end 218 of the stop sheath 214. A pin 220 may be received at least partially in the hole 216. At least a portion of the pin 220 may extend from the hole 216 so that when the shaft 202 is received at least partially extending through the stop sheath 214, the pin 220 may engage the distal end 218 of the stop sheath 214. Engagement between the pin 220 and the distal end 218 of the stop sheath 214 may limit and/or control sliding movement and/or axial position of the shaft 202 relative to the stop sheath 214.

In addition to limiting and/or controlling sliding movement and/or axial position of the shaft 202 relative to the stop sheath 214, the pin 220 may travel along the distal end 218 of the stop sheath 214 during rotation of the shaft 202. As the pin 220 travels along the distal end 218 of the stop sheath 214, the axial position of the shaft 202 relative to the stop sheath 214 may vary corresponding to the profile of the distal end 218 of the stop sheath 214. Variation of the axial position of the shaft 202 relative to the stop sheath 214 may correspondingly vary characteristics of an excision site created using the excision tool 200.

According to a further aspect, an excision tool consistent with the present disclosure may be employed in connection with an end-on application and/or procedure. As compared to the retrograde procedure described in detail above, an end-on procedure may include excision of at least a portion of an articular surface from a location in front of the articular surface. According to such an embodiment the force applied to the cutter may be directed toward the articular surface. For example, the cutter may be engaged with the central shaft and may be positioned adjacent to the articular surface with the central shaft extending outwardly away from the articular surface. The articular surface may be excised by rotating the cutter, such as by rotating the central shaft, and applying a force urging the cutter into the articular surface. For example, the force may be applied by pushing the central shaft, i.e., applying a compressive force to the shaft. In this manner, urging the cutter into the articular surface may include pushing the cutter into the articular surface rather than pulling the cutter into the articular surface, as during a retrograde procedure.

Similar to previously discussed retrograde procedures, during an end-on procedure the cutter may be rotated in a plane that is not perpendicular to the axis of the central shaft. That is, the cutter may be tilted relative to the central shaft. In an end-on procedure, as in a retrograde procedure, the range of tilt of the cutter relative to the central shaft may include 0 degrees, i.e., the cutter may be oriented normal to the central shaft. As with a retrograde procedure, the excision site may have a cross-sectional geometry corresponding to the intersection of the rotating cutter and the articular surface, and may further be projected along the axis of the applied force, e.g., along the axis of the central shaft. The orientation of the cutter, and therefore, the geometry of the excision site, may be controlled by the interaction of the cutter and the articular surface. For example, the cutter may be rotated in contact with the articular surface and the tilt angle of the cutter relative to the central shaft may be controlled and/or influenced by the geometry of the articular surface. Additionally, and/or alternatively, the tilt angle of the cutter relative to the central shaft, and/or relative to the articular surface, may be controlled and/or influenced by a sheath or guide which may contact at least a portion of the cutter. The sheath and/or guide may influence the tilt angle of the cutter in a similar manner as discussed with reference to a retrograde procedure.

Operation of the excision tool during an end-on procedure may be guided and/or controlled in a similar manner as discussed with respect to a retrograde procedure. For example, a drill guide may be employed to control and/or influence the orientation of the central shaft. Additionally, and/or alternatively, the orientation of the central shaft may controlled by controlling and/or influencing the orientation of a drive motor, e.g., in a generally free-hand manner. Furthermore, features may be provided in the articular surface to control and/or influence the orientation of the central shaft and/or excision site. For example, a passage or hole may extend into the bone behind the articular surface. At least a portion of the central shaft may be received in the passage or hole and may at least in part guide and/or direct the central shaft. These, and various additional and/or alternative techniques for guide and/or controlling the operation of an excision tool, may be used alone and/or in combination with one or more additional techniques.

The orientation of the cutter may also be influenced and/or controlled by a guide etc. For example, a guide may be provided with at least a portion of the guide being in contact with at least a portion of the cutter. Contact between the cutter and the guide may control and/or influence the angle of the cutter. Additionally, the guide may have a contact surface configured to provide a varying tilt angle of the cutter through each cycle of rotation of the cutter.

As discussed with reference to FIGS. 1 and 2, the internal passage and the slot in the central shaft may extend from the opening through the central shaft away from the adjacent and/or distal end of the central shaft. Consistent with the foregoing description of an exemplary end-on procedure, a cutting force applied to the cutter via the central shaft may urge the cutter away form the distal end and/or the end adjacent to the opening. The discussed alternative configuration of the internal passage and of the slot may accommodate an end-on procedure. Similar modifications may be employed as necessary in connection with alternative embodiments of the excision tool. Such modifications will be readily appreciated.

An excision tool, and the associated method, consistent with the present disclosure may permit an excision site to be formed in an articular surface from a retrograde location and/or from an end-on location. The cutter may be, at least initially, oriented in a plane that is not normal to the axis of a shaft which may rotationally drive the cutter. This may allow the cutter of the excision tool to, at least initially, be oriented in a plane relative to the articular surface and/or in a plane between cooperating articular surfaces of a joint. Such initial orientation of the cutter may minimize and/or eliminate the need to separate and/or dislocate a joint in order to provide an implant site in one of the articular surfaces. Furthermore, the tilted orientation of the cutter relative to the shaft may improve access to remote and/or obscured regions of the articular surface. Additionally, and/or alternatively, initially orienting the cutter of the excision tool in a plane between the cooperating articular surfaces may allow an excision site to be formed in one of the articular surfaces without gouging the cooperating articular surface, as may occur for a cutter that is fixed in a plane normal to the shaft rotationally driving the cutter.

The embodiments describe herein have been set forth as examples for illustrating the various aspects, features, and advantages of the present invention. The various features and aspects of the individual embodiments are susceptible to combination with features and aspects of the various other embodiments. Similarly, the embodiments, as well as the features and aspects thereof, are susceptible to variation and modification without departing from the spirit of the present invention. Accordingly, the described and illustrated embodiments should not be construed as limiting the scope of the present invention.

What is claimed is:

1. An excision tool for removing a portion of a patient's articular surface, said excision device comprising:
   a cutter comprising a ball coupling and a first and a second longitudinal member extending generally between said ball coupling and a first and second opposite end, respectively, of said cutter, wherein at least a portion of each of said first and second longitudinal member comprises a cutting edge and wherein said ball coupling has a cross-sectional dimension which is greater than a cross-sectional dimension of said first and said second longitudinal members; and
   a shaft comprising a proximal and a distal end, wherein said shaft comprises:
      an opening adjacent to said distal end of said shaft, said opening having a cross-sectional dimension greater than said cross-sectional dimension of said ball coupling such that said opening is configured to receive said first end and said ball coupling of said cutter;
      an internal passageway extending from said opening towards said distal end of said shaft, said internal passageway having an internal diameter less substantially corresponding to said cross-sectional dimension of said ball coupling and less than said cross-sectional dimension of said opening; and
      a slot extending along said internal passageway and having a cross-sectional dimension less than said cross-sectional dimensions of said ball coupling and said opening and greater than said cross-sectional dimensions of said first and second longitudinal members such that said first and second longitudinal members are configured to extend through said slot and beyond an outer surface of said shaft;

wherein said ball coupling of said cutter is configured to be received through said opening and into said internal passageway and translated towards said distal end of said shaft such that said ball coupling engages said internal passageway and said cutter is rotatable within a longitudinal axis of said shaft and tiltable relative to said longitudinal axis of said shaft when said cutter is disposed against said patient's articular surface.

2. An apparatus according to claim 1, wherein said cutter is configured to be removably coupled to said shaft.

3. An apparatus according to claim 1, further comprising a cap configured to be coupled to distal end of said shaft, said cap defining a closed end of said internal passageway.

4. An apparatus according to claim 1, wherein said first and said second ends of said cutter are tapered.

5. A system for excising a portion of an articular surface, said system comprising:
- a stop sheath comprising an axial bore;
- a central shaft rotatably and slidably receivable in said bore, said shaft comprising a proximal and a distal end;
- a cutter comprising a ball coupling and a first and a second longitudinal member extending generally between said ball coupling a first and second opposite end, respectively, of said cutter, wherein at least a portion of each of said first and second longitudinal member comprises a cutting edge and wherein said ball coupling has a cross-sectional dimension which is greater than a cross-sectional dimension of said first and said second longitudinal members; and
- a shaft comprising a proximal and a distal end, wherein said shaft comprises:
  - an opening adjacent to said distal end of said shaft, said opening having a cross-sectional dimension greater than a cross-sectional dimension of said ball coupling such that said opening is configured to receive said first end and said ball coupling of said cutter;
  - an internal passageway extending from said opening towards said distal end of said shaft, said internal passageway having an internal diameter less substantially corresponding to said cross-sectional dimension of said ball coupling and less than said cross-sectional dimension of said opening; and
  - a slot extending along said internal passageway and having a cross-sectional dimension less than said cross-sectional dimensions of said ball coupling and said opening and greater than said cross-sectional dimensions of said first and second longitudinal members such that said first and second longitudinal members are configured to extend through said slot and beyond an outer surface of said shaft;
  - wherein said ball coupling of said cutter is configured to be received through said opening and into said internal passageway and translated towards said distal end of said shaft such that said ball coupling engages said internal passageway and said cutter is rotatable within a longitudinal axis of said central shaft and is tiltable relative to said a longitudinal axis of said central shaft when said cutter is disposed against said articular surface.

6. A system according to claim 5, wherein said stop sheath is configured to be at least partially disposed in an access tunnel defined in a bone, said stop sheath being axially translatable within said access tunnel.

7. A system according to claim 6, wherein said stop sheath comprises an external thread configured to threadably engage bone defining an access tunnel.

8. A system according to claim 6, wherein said central shaft is configured to be axially translatable with said stop sheath.

9. A system according to claim 5, wherein said cutter comprises a bearing surface configured to travel along a distal end of said stop sheath.

10. An apparatus according to claim 5, wherein said first and said second ends of said cutter are tapered.

* * * * *